US012594346B2

(12) United States Patent
Garcia et al.

(10) Patent No.: US 12,594,346 B2
(45) Date of Patent: Apr. 7, 2026

(54) CROSSLINKED HYDROGEL FOR IMMUNE CHECKPOINT BLOCKADE DELIVERY

(71) Applicants: GEORGIA TECH RESEARCH CORPORATION, Atlanta, GA (US); UNIVERSITY OF LOUISVILLE RESEARCH FOUNDATION, INC., Louisville, KY (US)

(72) Inventors: Andres J. Garcia, Atlanta, GA (US); Maria M. Coronel, Atlanta, GA (US); Haval Shirwan, Columbia, MO (US); Esma S. Yolcu, Columbia, MO (US)

(73) Assignees: Georgia Tech Research Corporation, Atlanta, GA (US); University of Louisville Research Foundation, Inc., Louisville, KY (US)

( * ) Notice: Subject to any disclaimer, the term of this patent is extended or adjusted under 35 U.S.C. 154(b) by 622 days.

(21) Appl. No.: 18/015,232

(22) PCT Filed: Jul. 8, 2021

(86) PCT No.: PCT/US2021/040863

§ 371 (c)(1),
(2) Date: Jan. 9, 2023

(87) PCT Pub. No.: WO2022/011125

PCT Pub. Date: Jan. 13, 2022

(65) Prior Publication Data

US 2023/0256115 A1 Aug. 17, 2023

Related U.S. Application Data

(60) Provisional application No. 63/049,185, filed on Jul. 8, 2020.

(51) Int. Cl.

| | |
|---|---|
| ***A61K 47/69*** | (2017.01) |
| ***A61K 47/22*** | (2006.01) |
| ***A61K 47/60*** | (2017.01) |

(52) U.S. Cl.

CPC .......... *A61K 47/6903* (2017.08); *A61K 47/22* (2013.01); *A61K 47/60* (2017.08)

(58) Field of Classification Search

None

See application file for complete search history.

(56) References Cited

U.S. PATENT DOCUMENTS

| | | | |
|---|---|---|---|
| 6,022,951 | A | 2/2000 | Sano et al. |
| 2018/0275040 | A1 | 9/2018 | Kim et al. |
| 2020/0046780 | A1 | 2/2020 | Shirwan et al. |
| 2020/0085971 | A1 | 3/2020 | Kevlahan et al. |

OTHER PUBLICATIONS

Pahler et al., Characterization and Crystallization of Core Streptavidin, J Biol. Chem., 262: 13933-37 (1987).
Sano et al., Recombinant Core Streptavidins, J Blot Chem. 270(47): 28204-09 (1995).
Chilkoti et al., Site-directed mutagenesis studies of the high-affinity streptavidin-biotin complex: contributions of tryptophan residues 79, 108, and 120, Proc Natl Acad Sci, 92(5): 1754-58 (1995).
Reznik et al., Streptavidins with intersubunit crosslinks have enhanced stability, Nat Biotechnol, 14(8): 1007-11(1996).
Meyer et al., Reduced antibody response to streptavidin through site-directed mutagenesis, Protein Sci., 10: 491-503 (2001).
Hiller et al., Studies on the biotin-binding site of avidin. Minimized fragments that bind biotin. J Biochem, 278: 573-85 (1991).
Livnah et al., Three-dimensional structures of avidin and the avidin-biotin complex, Proc Natl Acad Sci USA 90: 5076-80 (1993).
Thompson et al., GenBank Accession No. X65082. Synthetic gene for streptavidin. https://www.ncbi.nlm.nih.gov/nuccore/x65082.
Argarana, et al., GenBank Accession No. X03591. Streptomyces avidinii gene for streptavidin. https://www.ncbi.nlm.nih.gov/nuccore/X03591.
Daryabari et al., GenBank Accession No. NM 205320. Gallus gallus avidin (AVD), mRNA. https://www.ncbi.nlm.nih.gov/nuccore/NM_205320.
Gope et al., GenBank Accession No. X05343. Chicken mRNA for avidin. https://www.ncbi.nlm.nih.gov/nuccore/X05343.
Keinanen et al., GenBank Accession No. Z21611. G.gallus avr1 gene. https://www.ncbi.nlm.nih.gov/nuccore/Z21611.
Keinanen et al., GenBank Accession No. Z21554. G.gallus avr2 gene. https://www.ncbi.nlm.nih.gov/nuccore/Z21554.
Ju et al., Fas(CD95)/FasL interactions required for programmed cell death after T-cell activation, Nature 373(6513): 444-448 (1995).
Yellen et al., High-dose rapamycin induces apoptosis in human cancer cells by dissociating mTOR complex 1 and suppressing phosphorylation of 4E-BP1, Cell Cycle, 10(22): 3948-3956 (2011).
International Preliminary Report on Patentability for International Application No. PCT/US2021/040863 dated Jan. 19, 2023, 6 pages.

(Continued)

*Primary Examiner* — Anand U Desai
(74) *Attorney, Agent, or Firm* — Meunier Carlin & Curfman LLC

(57) ABSTRACT

Disclosed are PD-L1 presenting compositions. The compositions may be used to effect immunomodulation in a variety of contexts. The compositions may be used to decrease rates of transplant rejection, including pancreatic islet cell transplantation. The compositions are useful for the treatment of type 1 diabetes.

20 Claims, 28 Drawing Sheets

Specification includes a Sequence Listing.

(56) References Cited

OTHER PUBLICATIONS

International Search Report and Written Opinion received in PCT/US2021/040863 mailed Oct. 28, 2021, 12 pages.
Extended European Search Report received in corresponding European Application No. 21837103.7, mailed Mar. 18, 2025.
Coronel et al: "C494.1 Synthetic Immunomodulatory Biomaterials to Improve Islet Graft Survival", Transplantation, vol. 102, No. Supplement 7, Jul. 1, 2018 (Jul. 1, 2018), p. S230, XP093251092, GB ISSN: 0041-1337.
Headen: "Microfluidics-Based Microgel Synthesis for Immunoisolation and Immunomodulation in Pancreatic Islet Transplantation", Dissertation, May 1, 2017 (May 1, 2017), XP055542432.

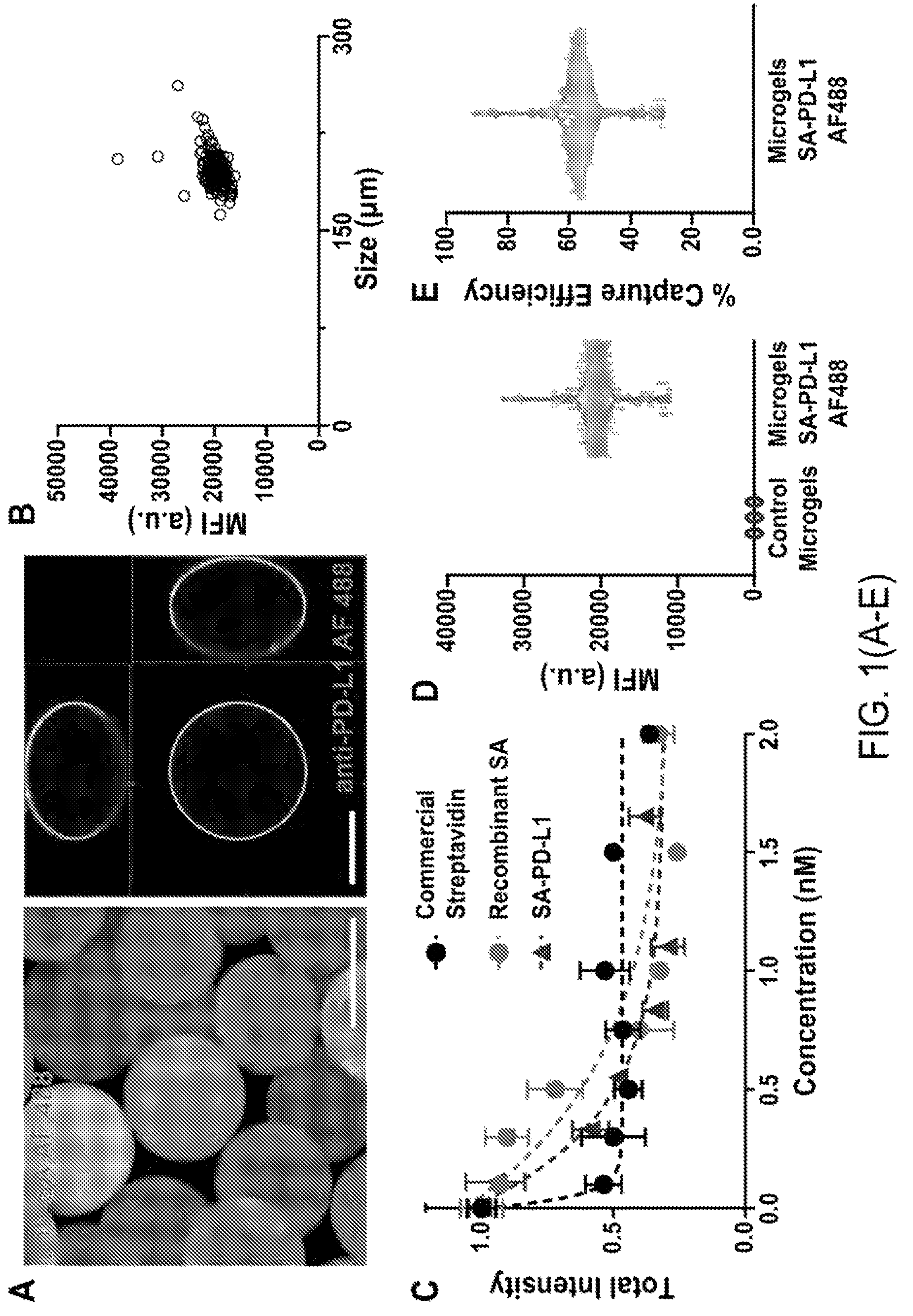
FIG. 1(A-E)

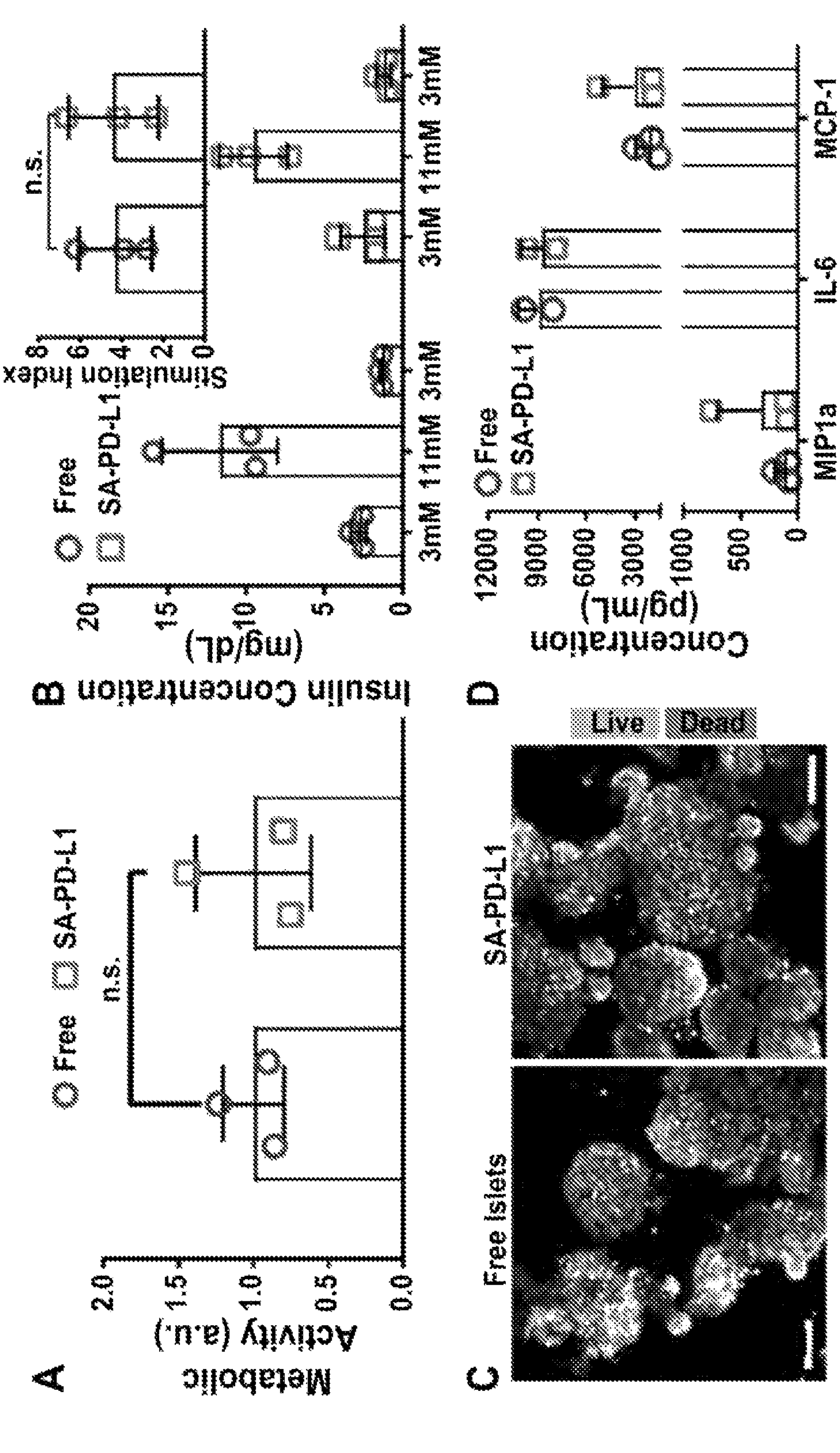
FIG. 2(A-D)

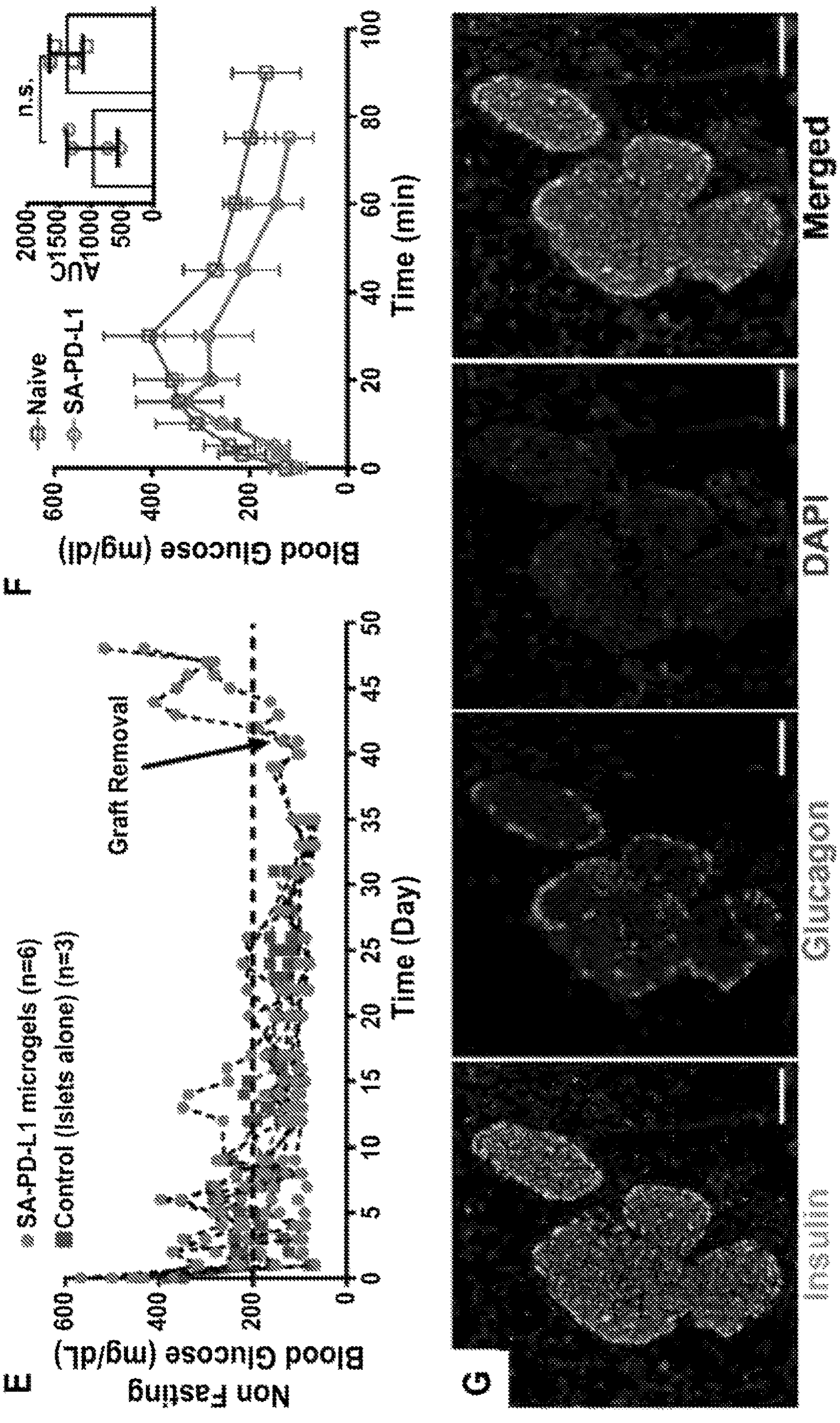
FIG. 2(E-G)

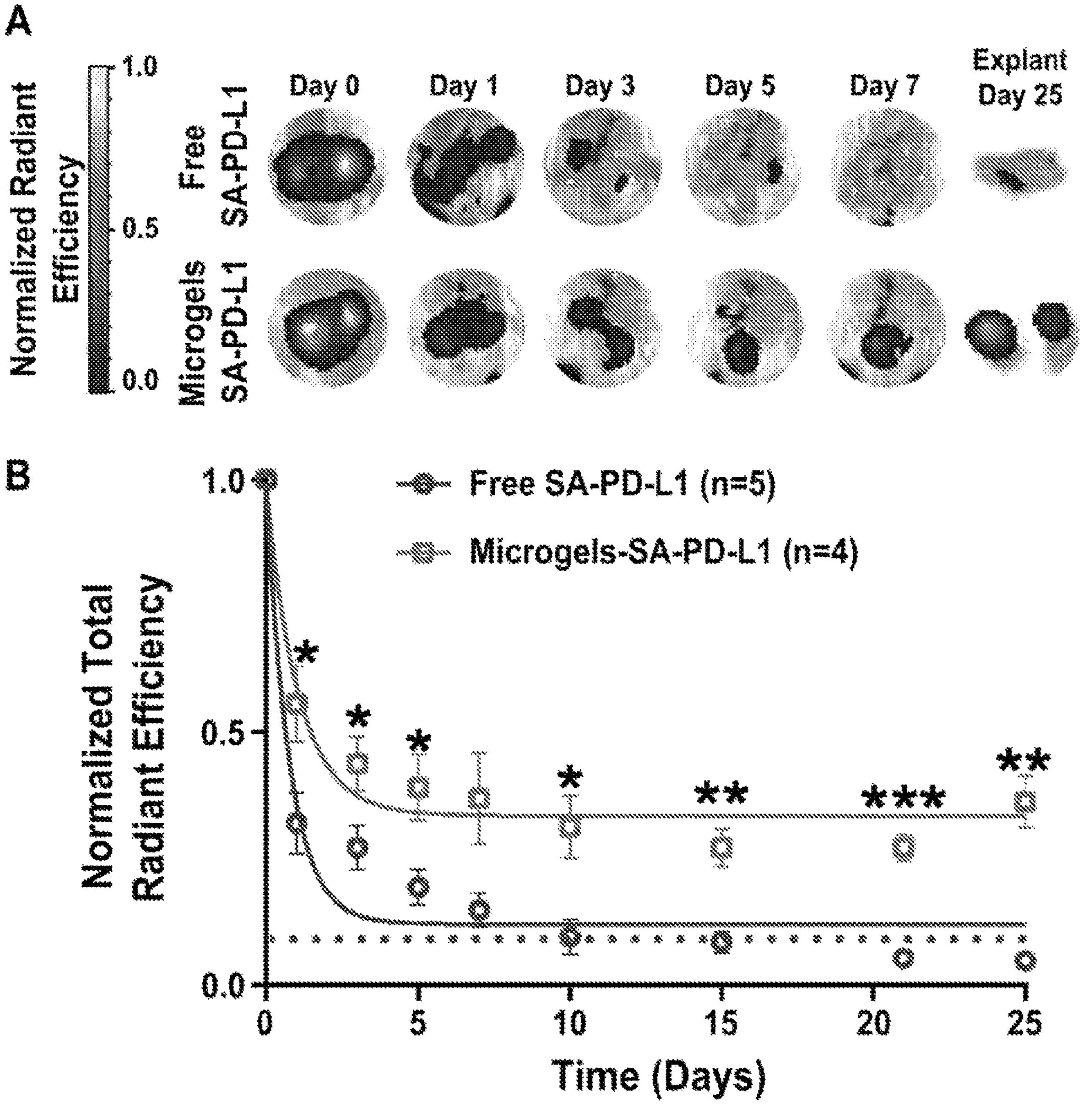
FIG. 3(A-B)

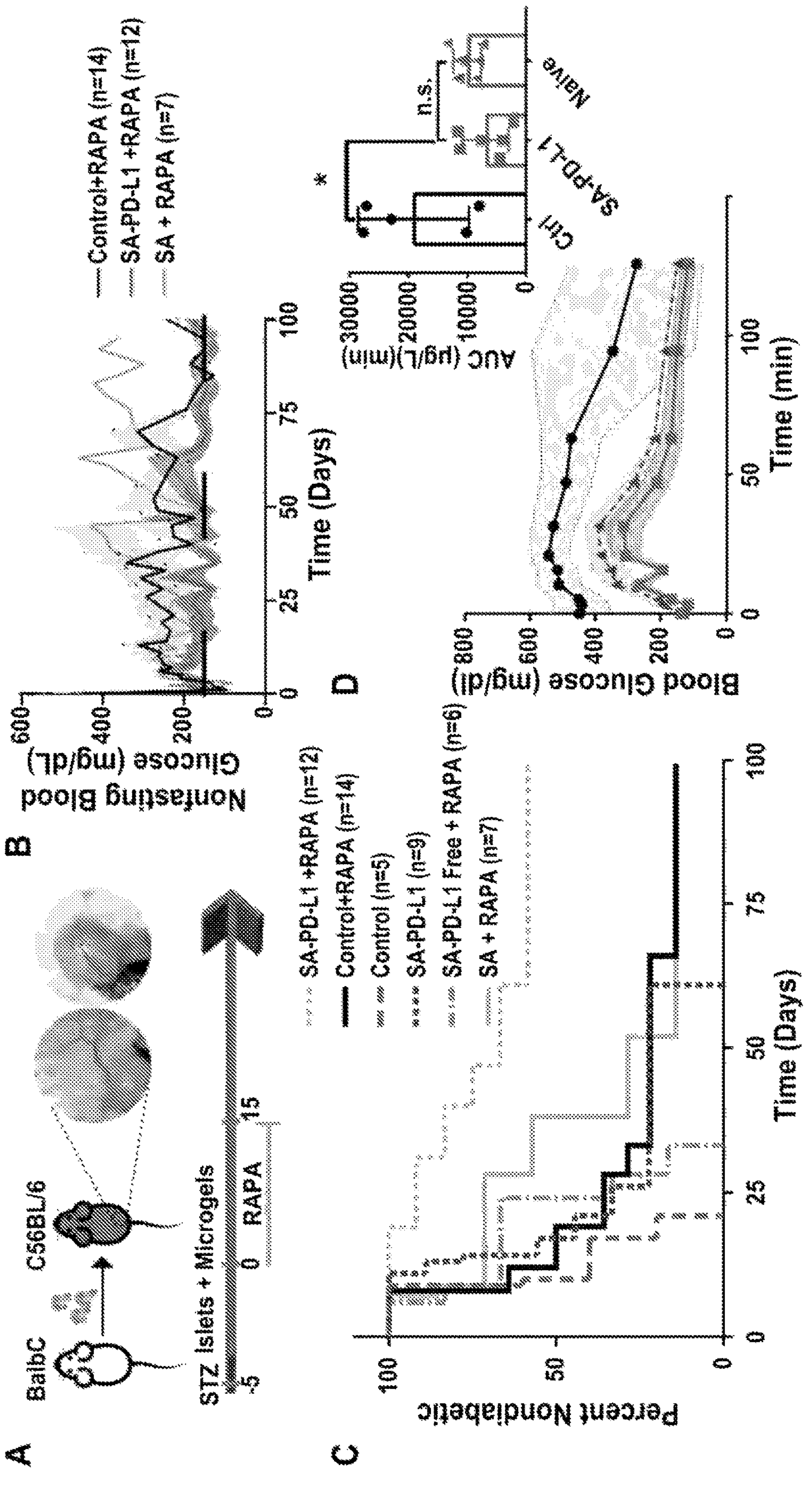
FIG. 4(A-D)

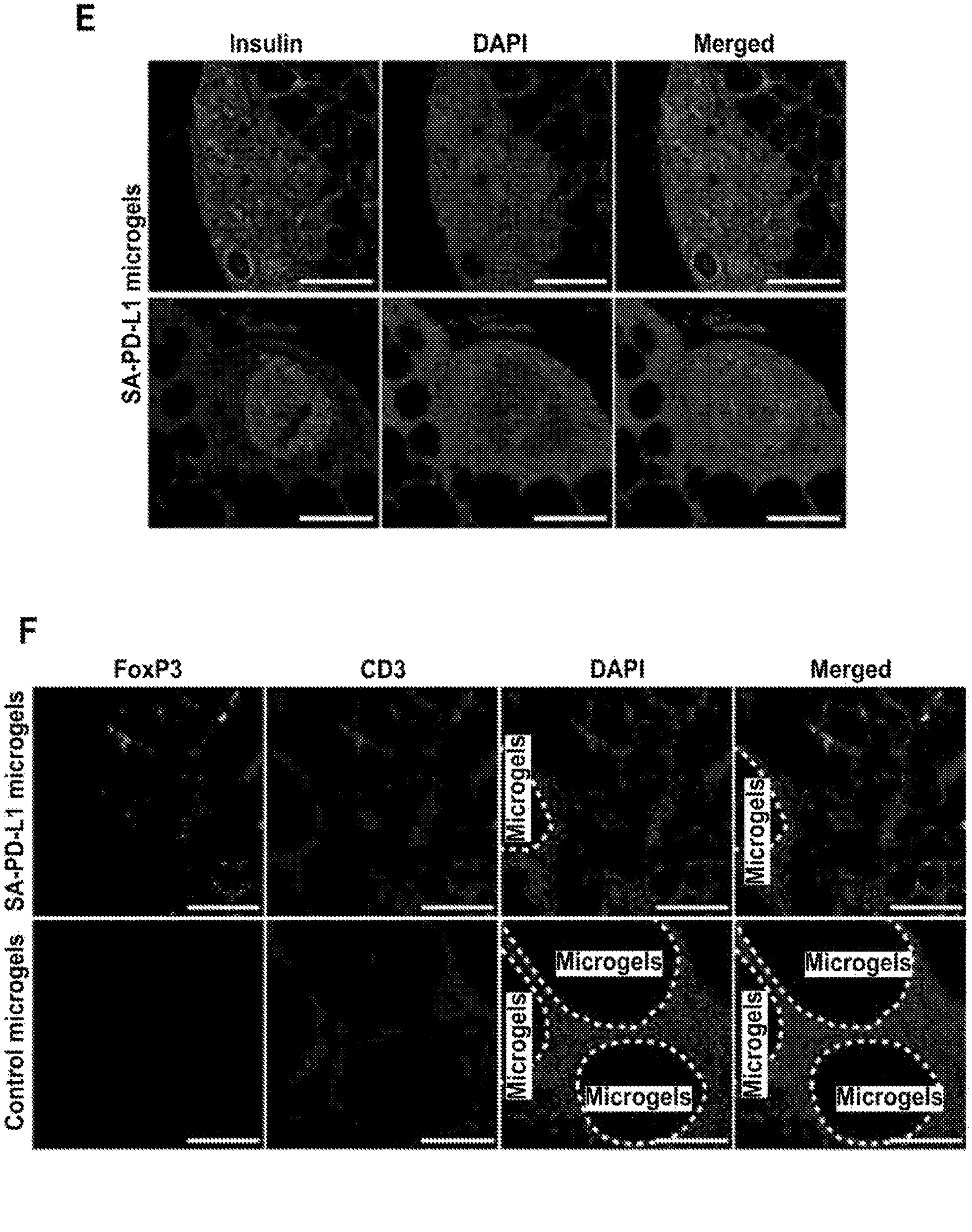
FIG. 4(E-F)

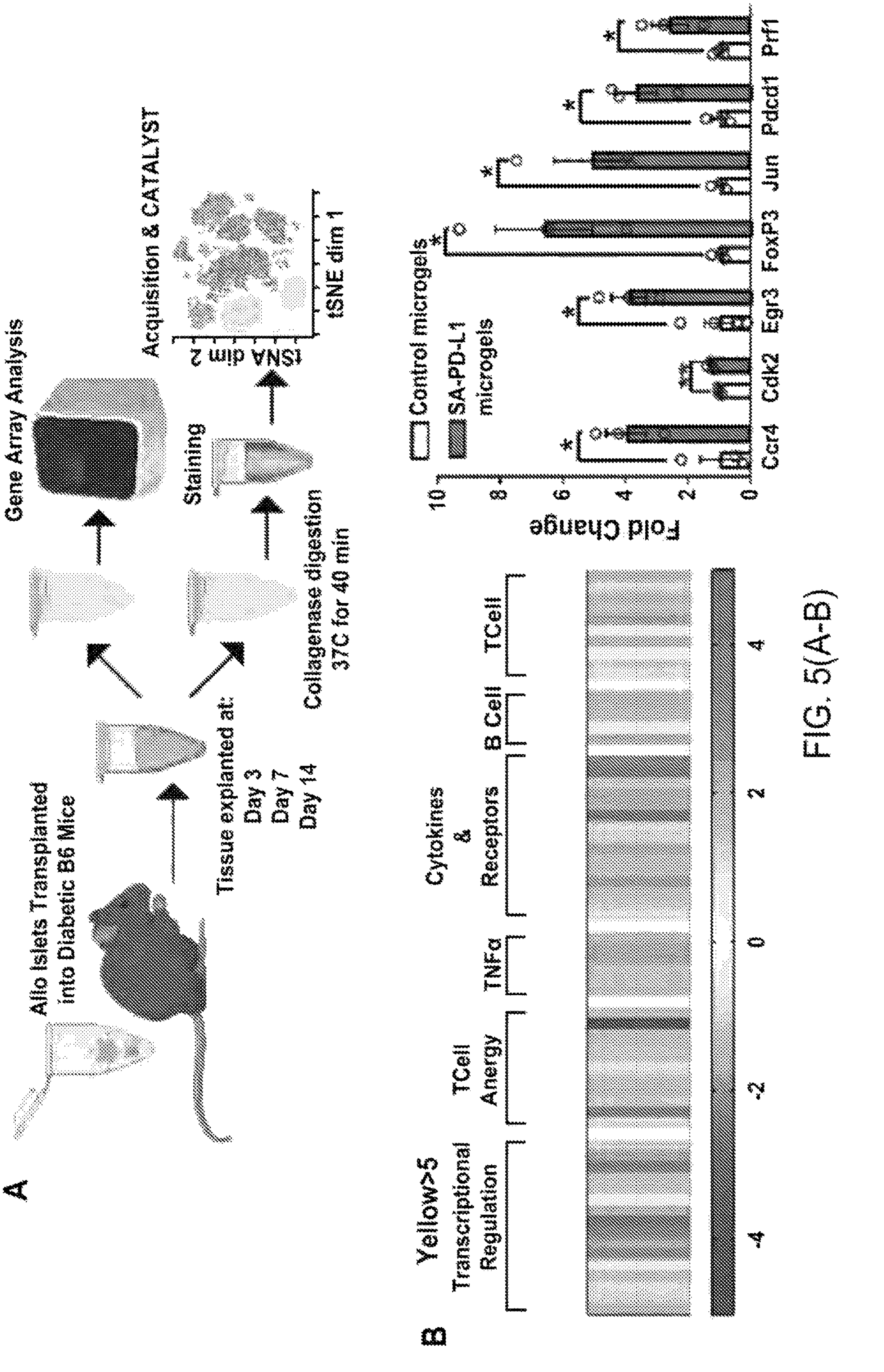
FIG. 5(A-B)

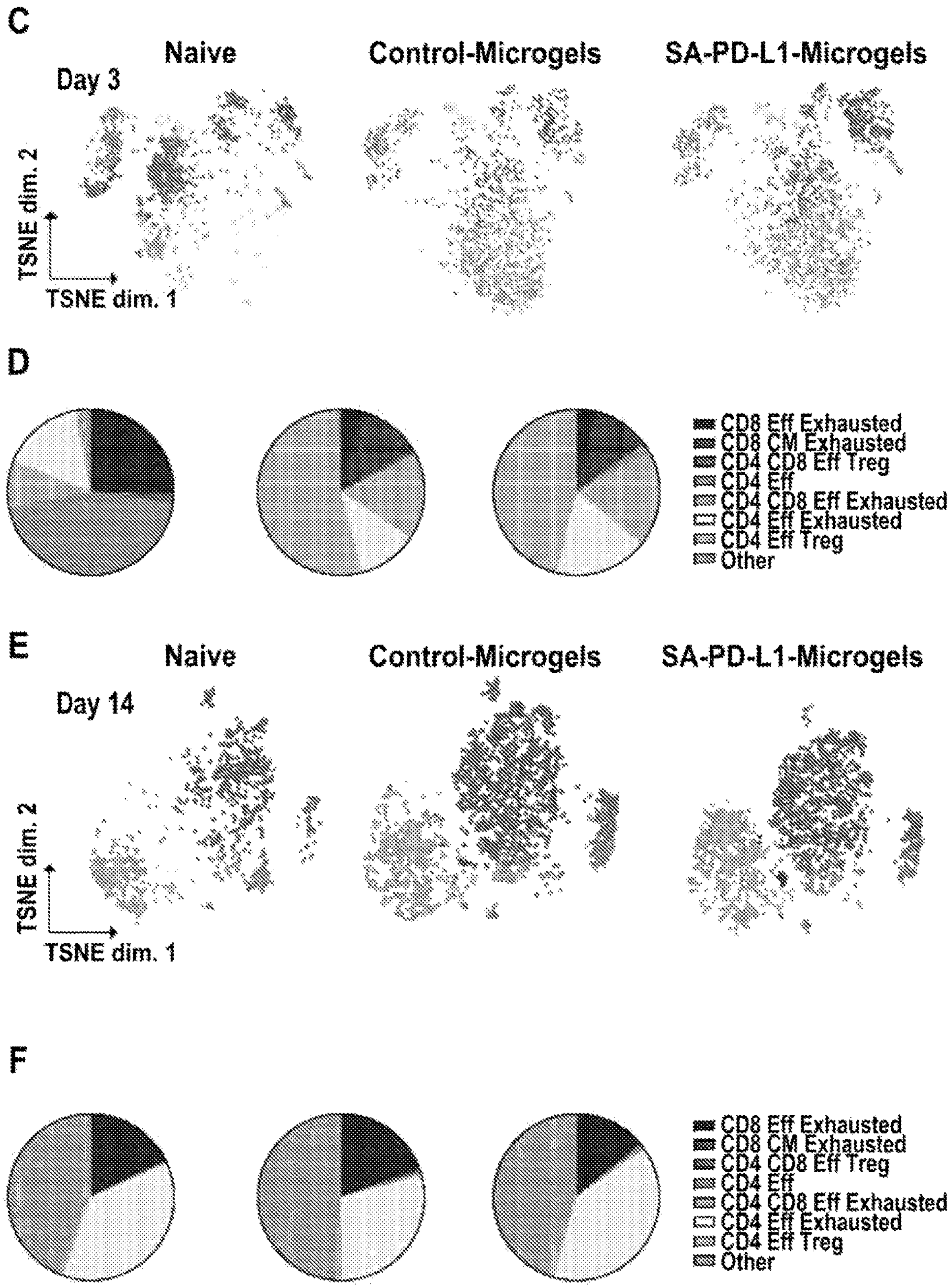
FIG. 5(C-F)

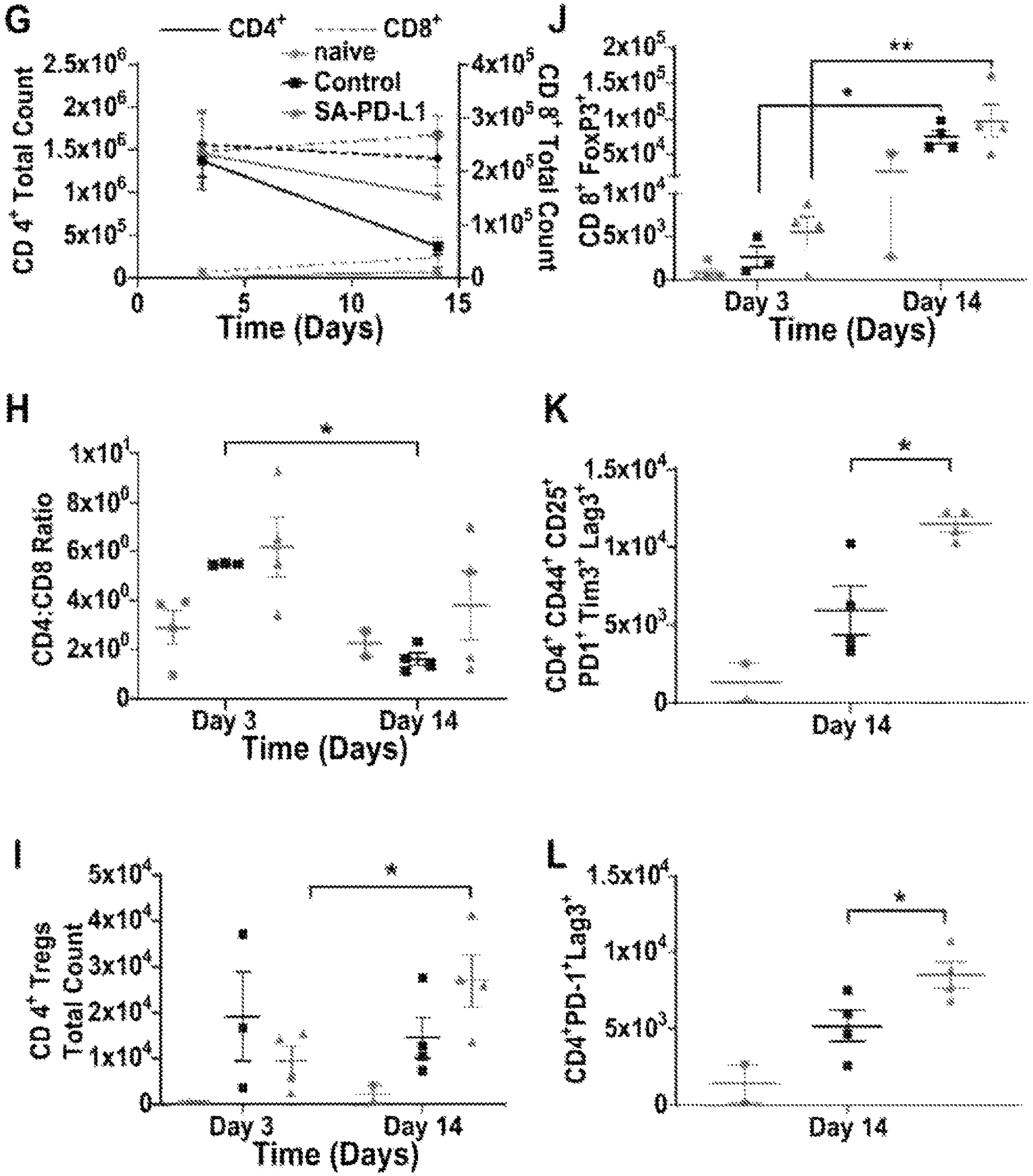
FIG. 5(G-L)

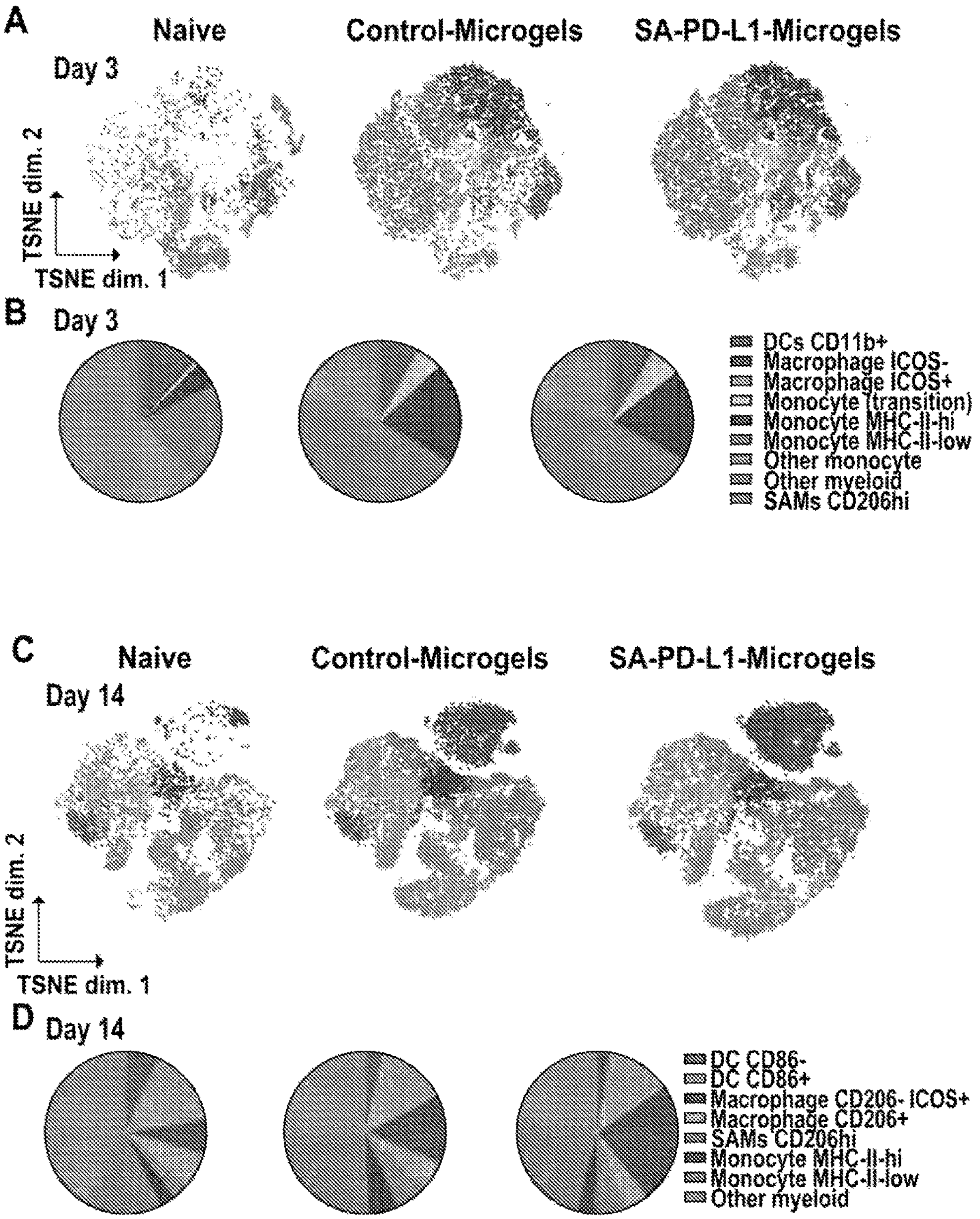
FIG. 6(A-D)

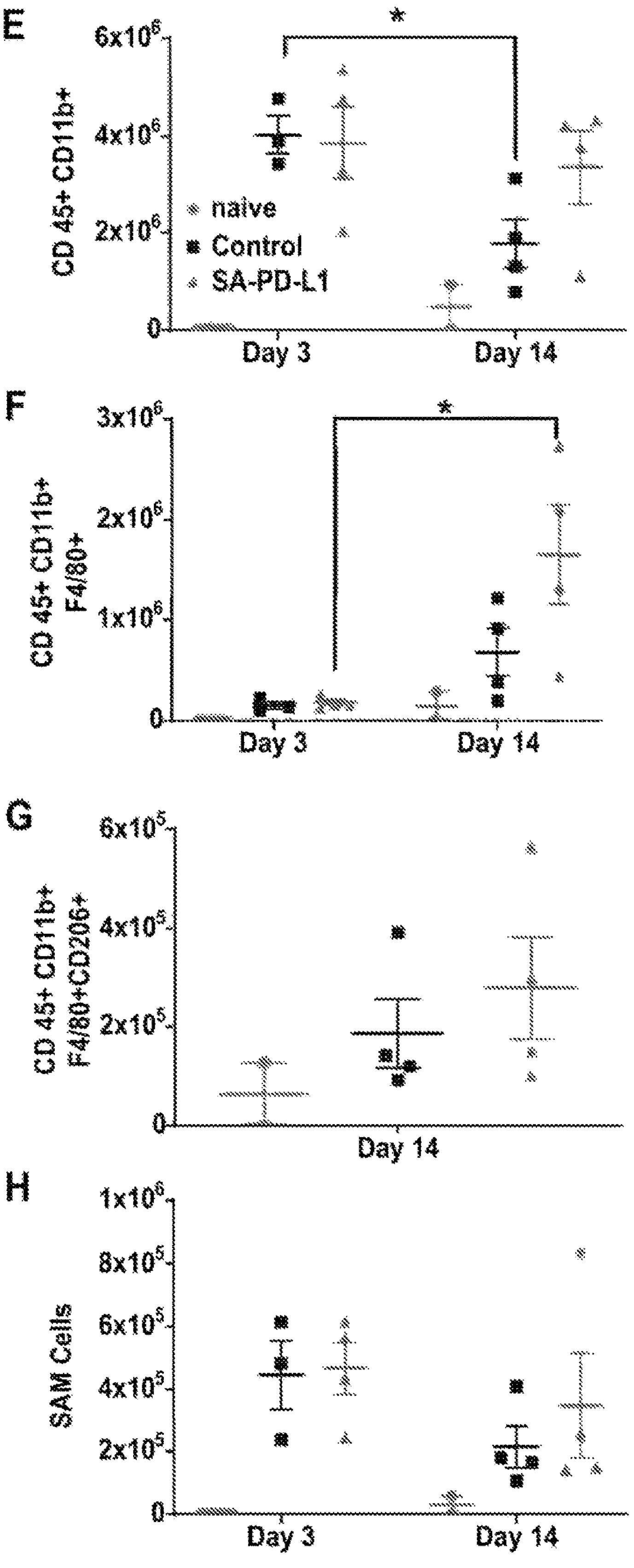
FIG. 6(E-H)

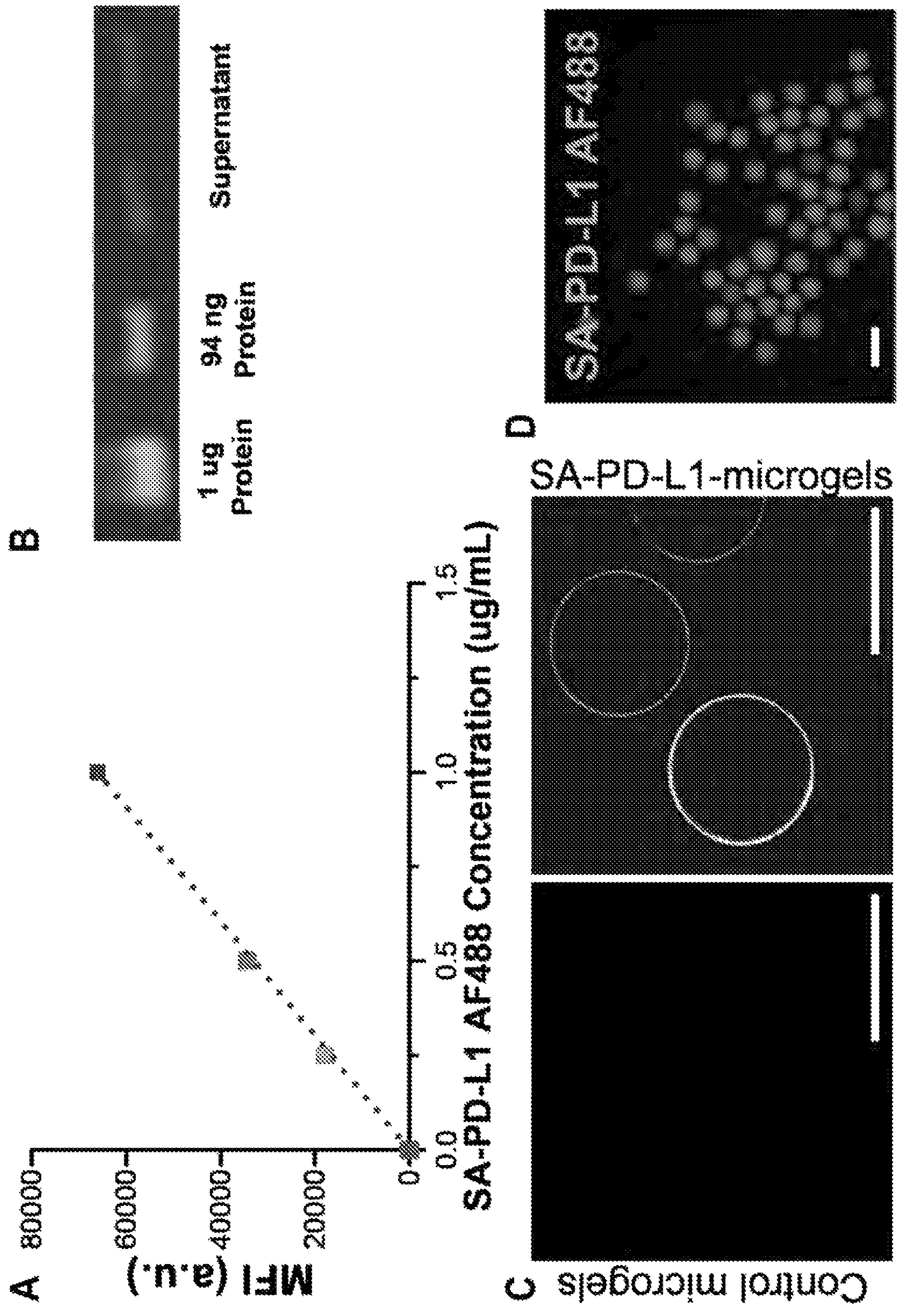
FIG. 7(A-D)

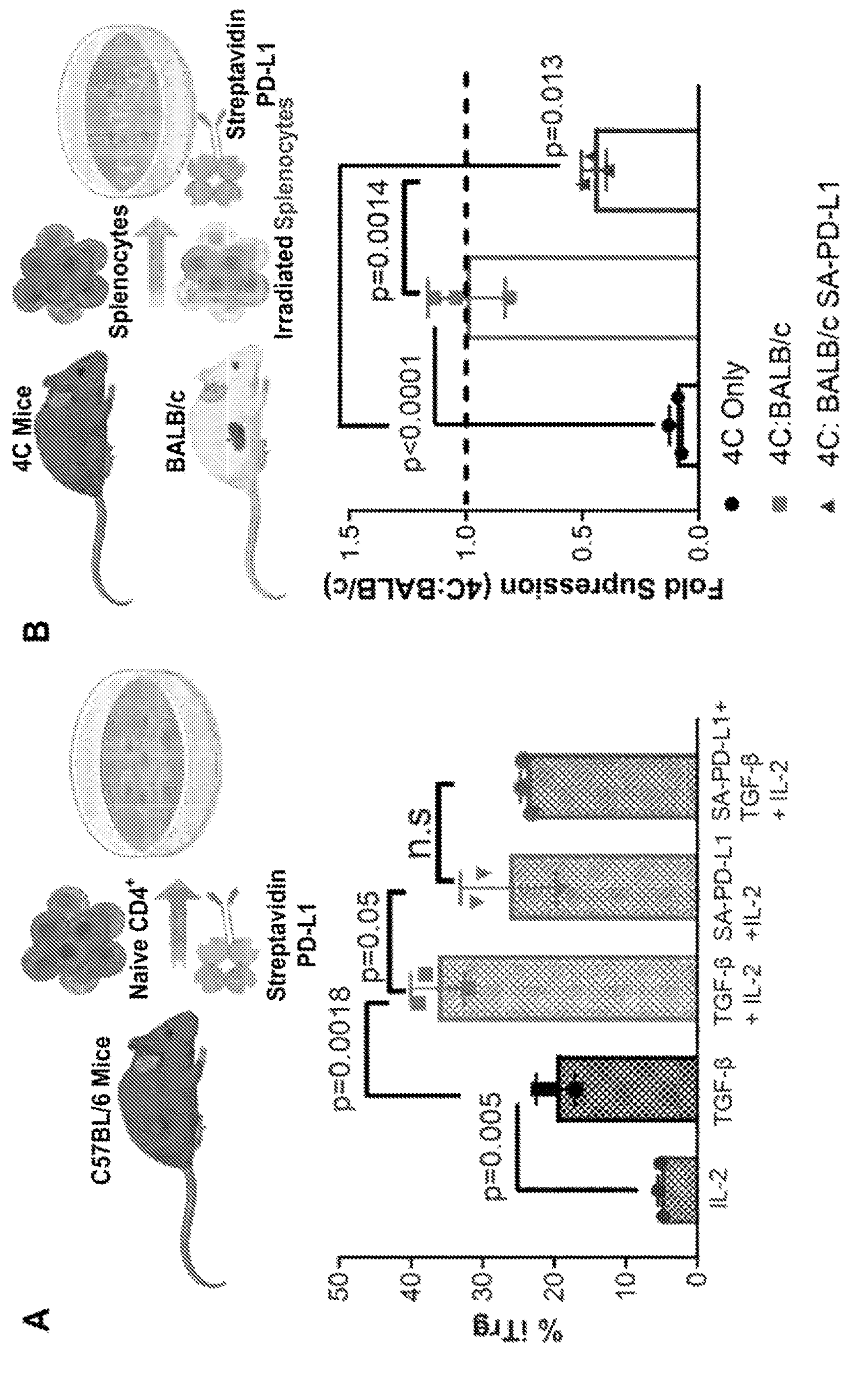
FIG. 8(A-B)

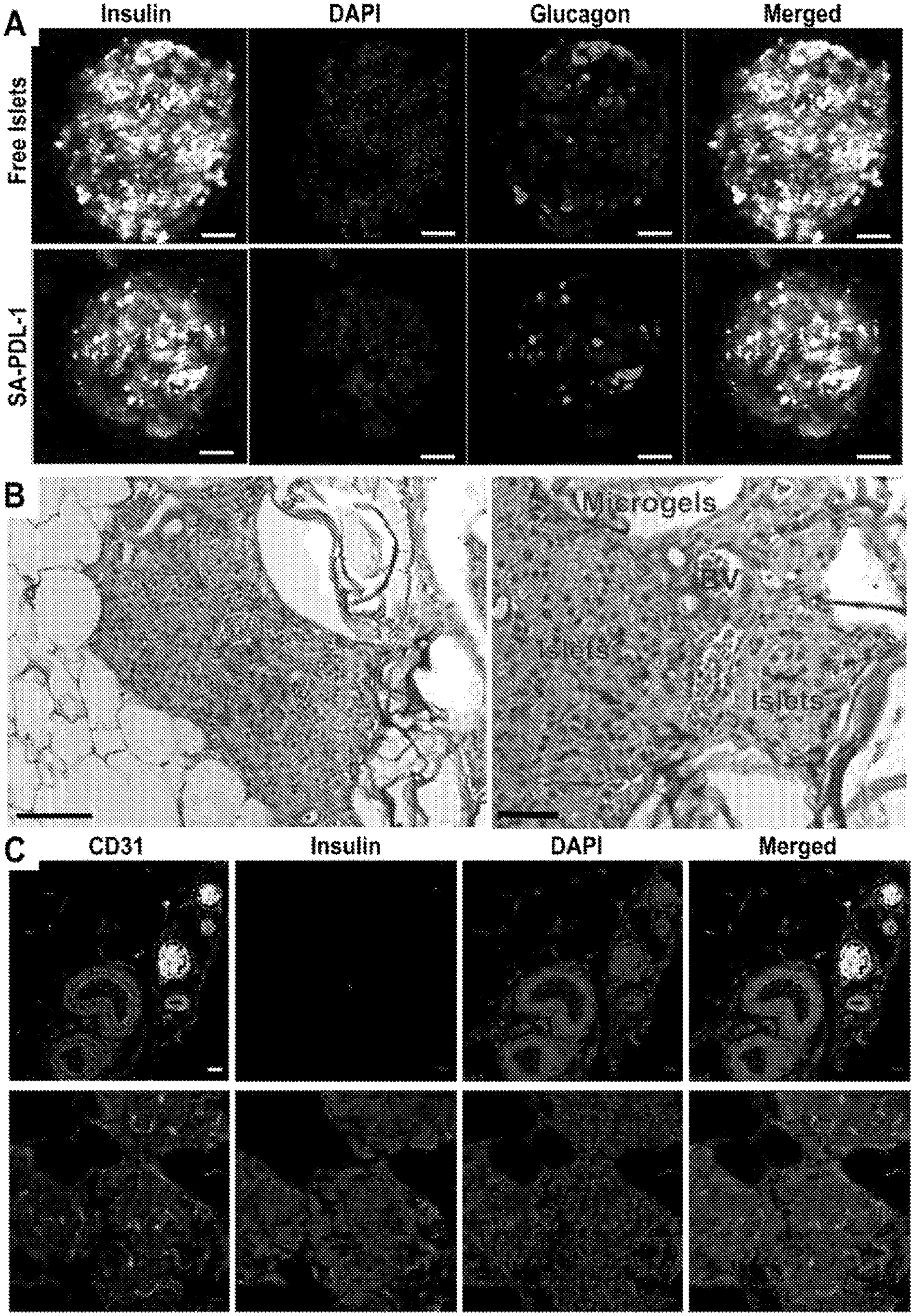
FIG. 9(A-C)

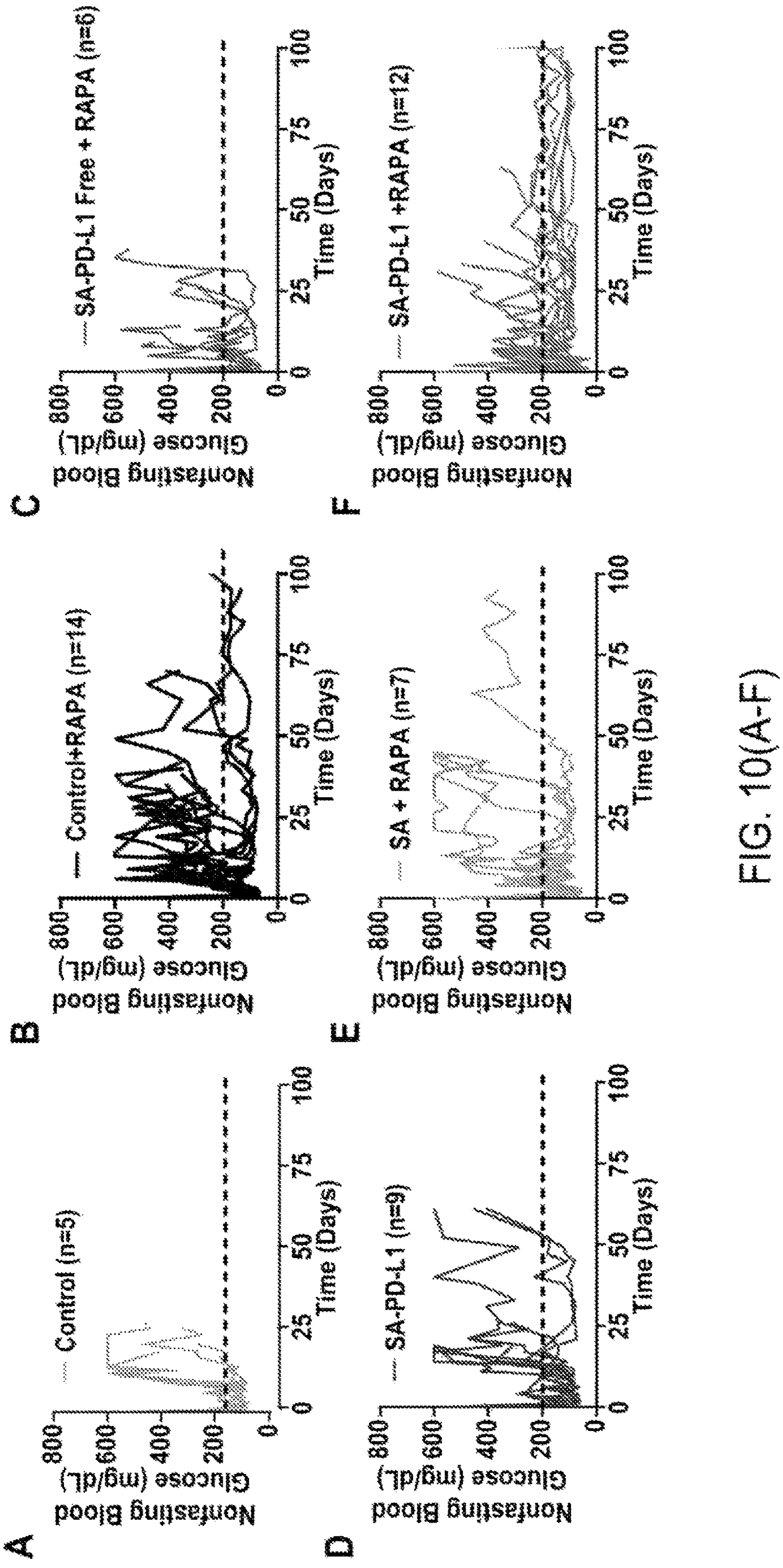
FIG. 10(A-F)

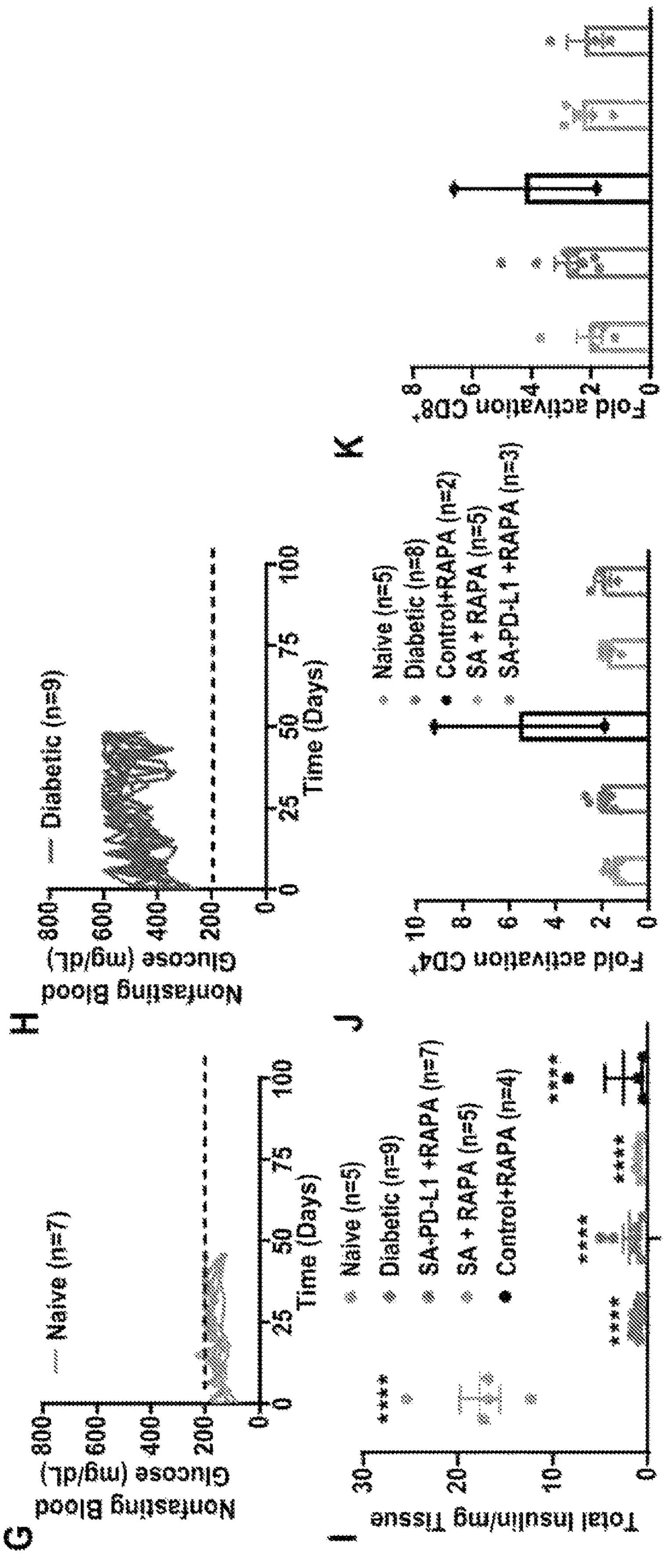
FIG. 10(G-K)

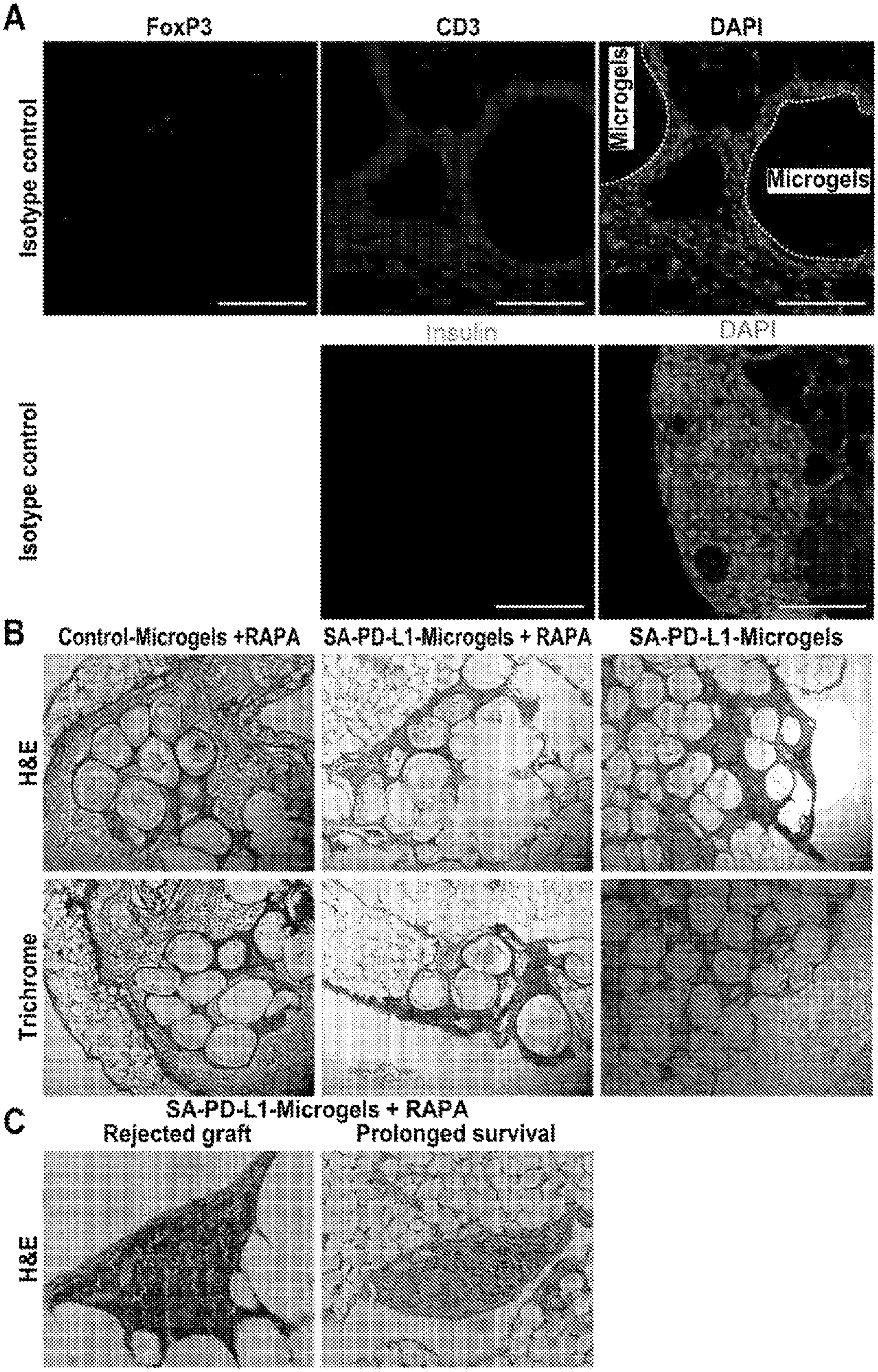
FIG. 11(A-C)

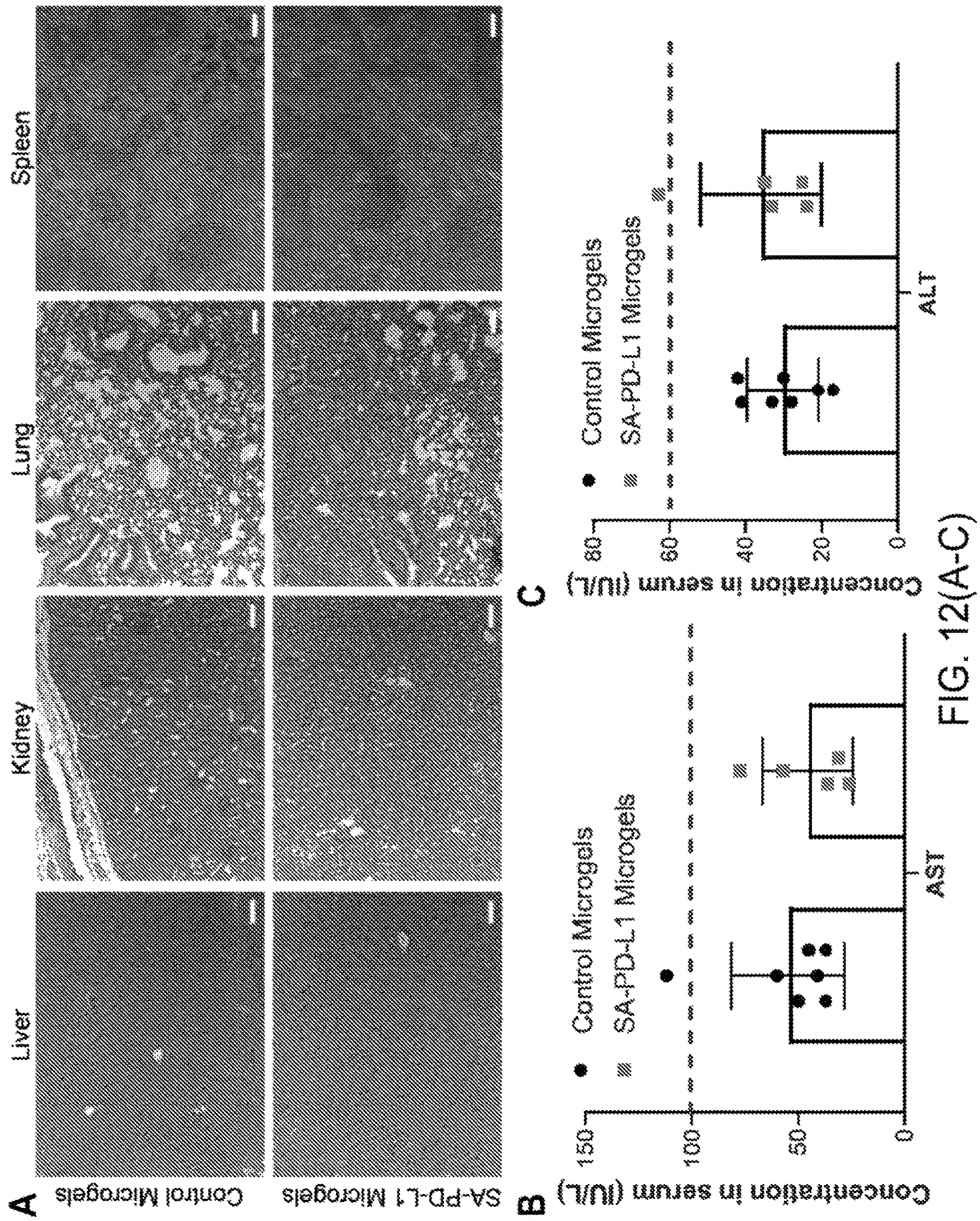
FIG. 12(A-C)

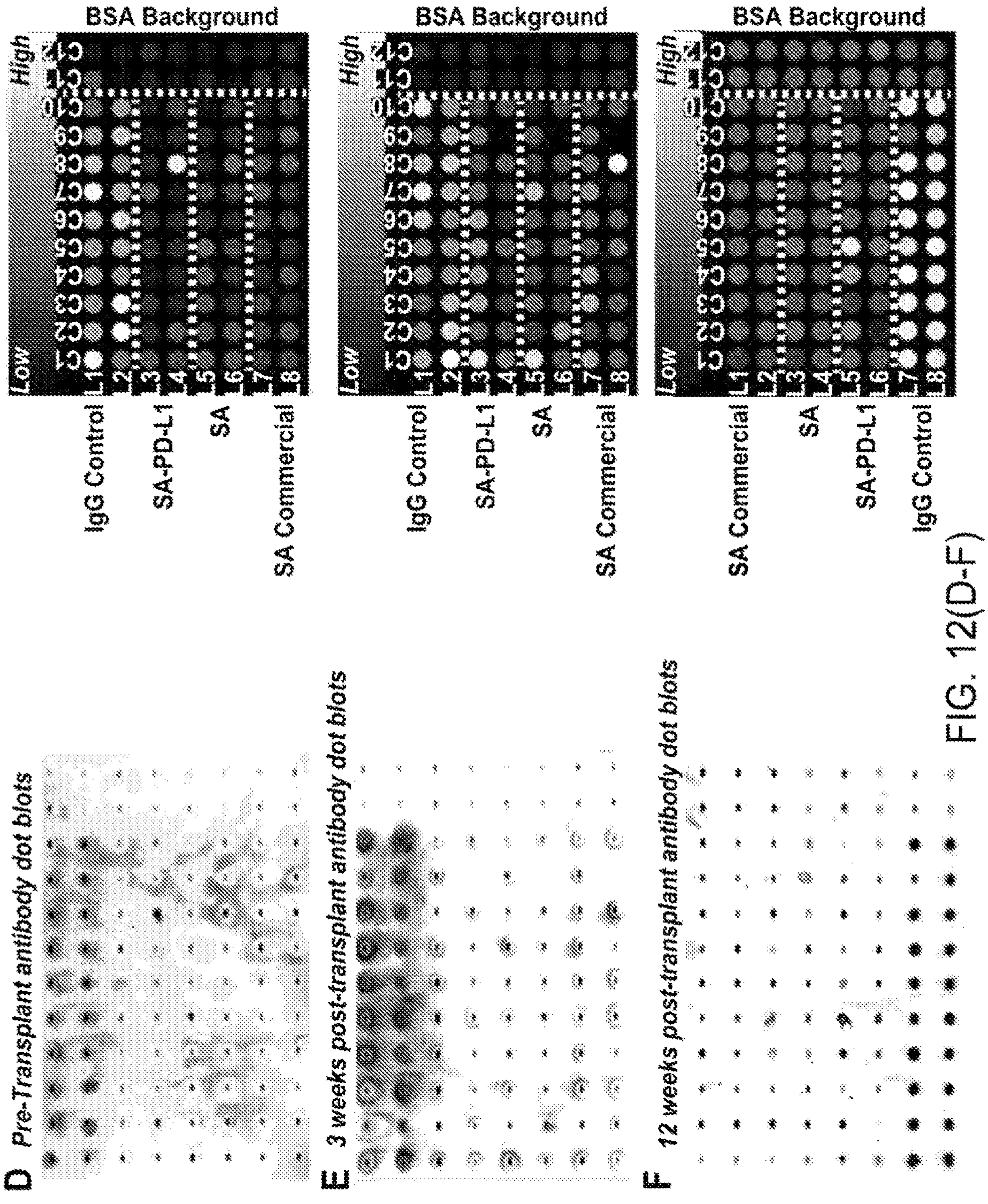
FIG. 12(D-F)

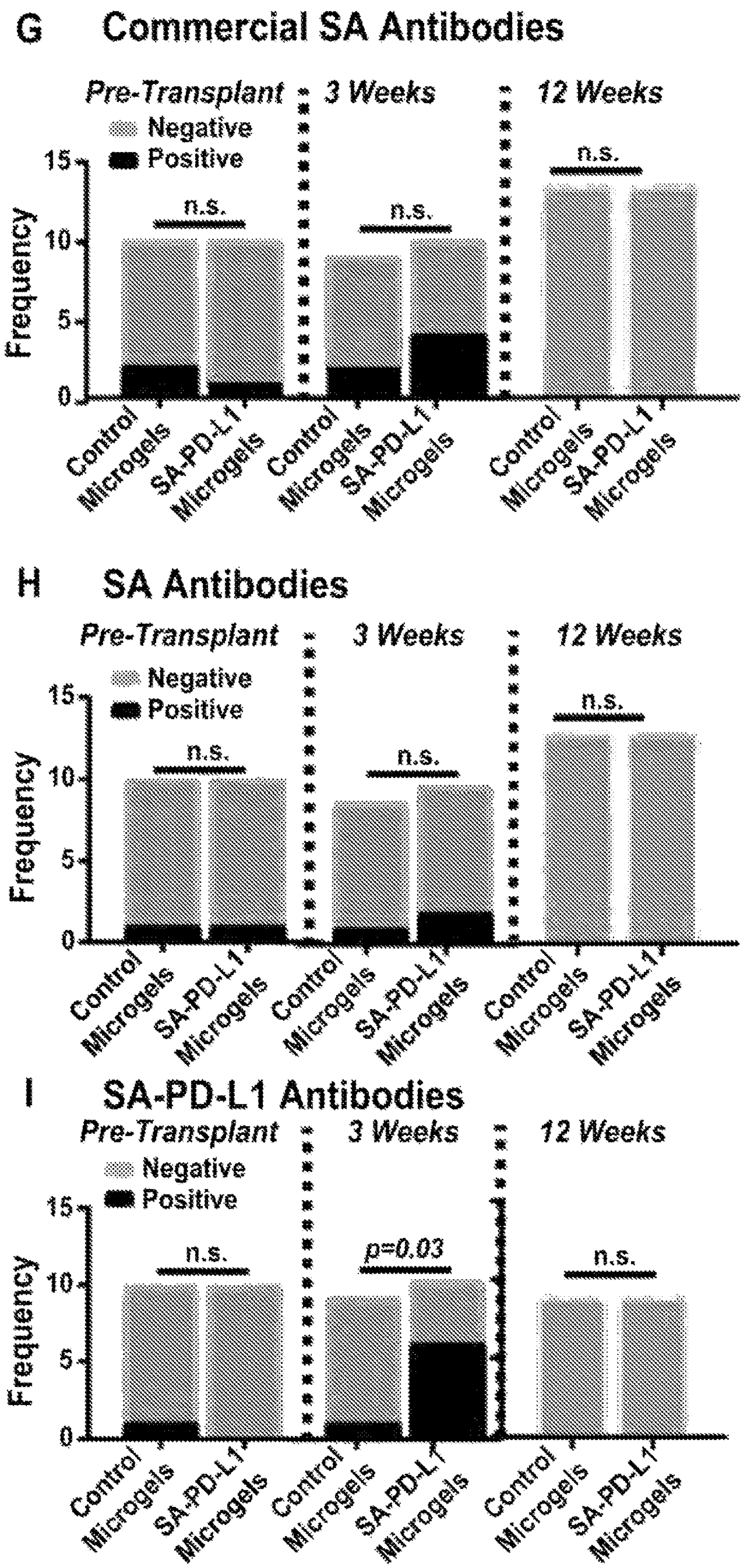
FIG. 12(G-I)

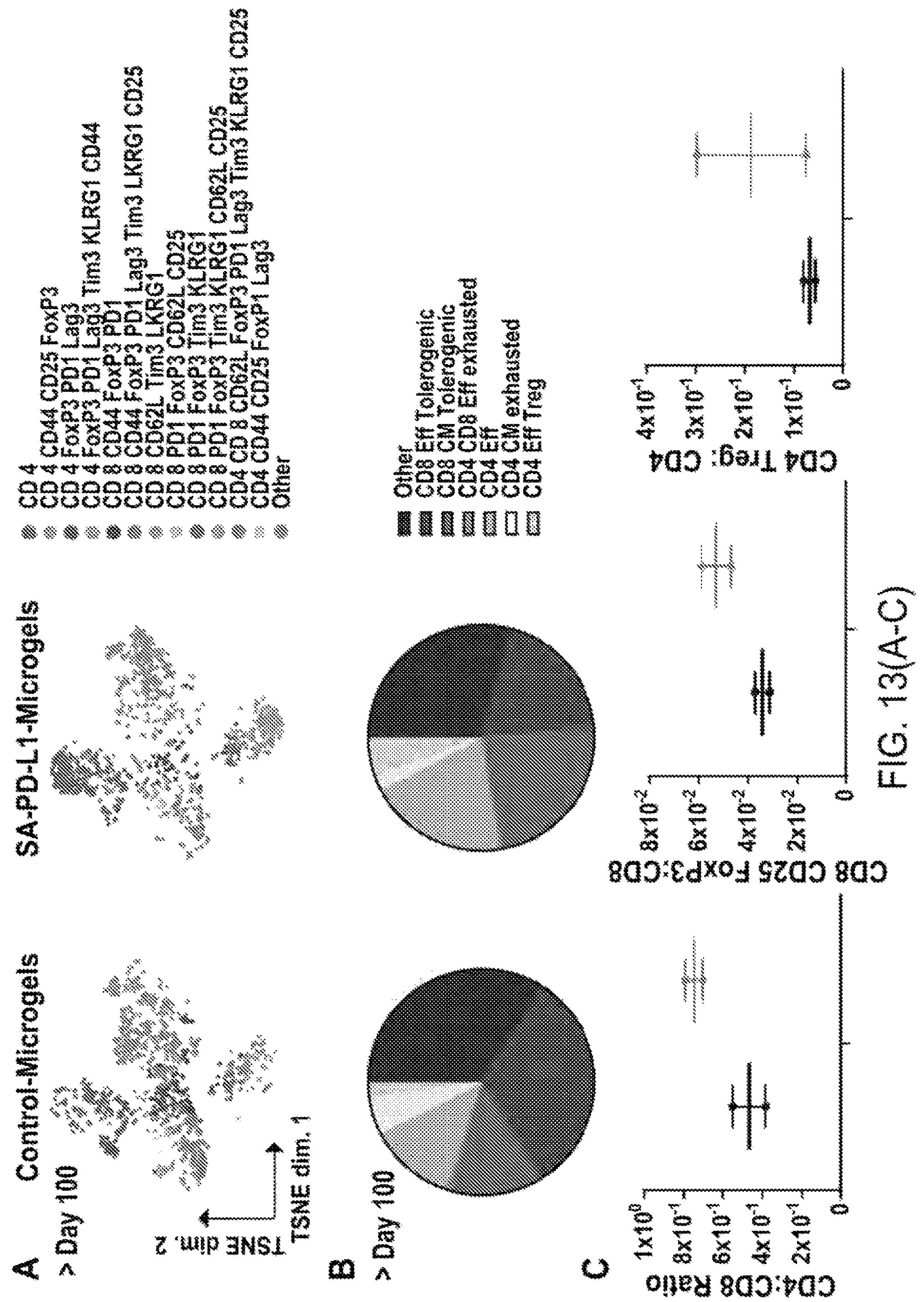
FIG. 13(A-C)

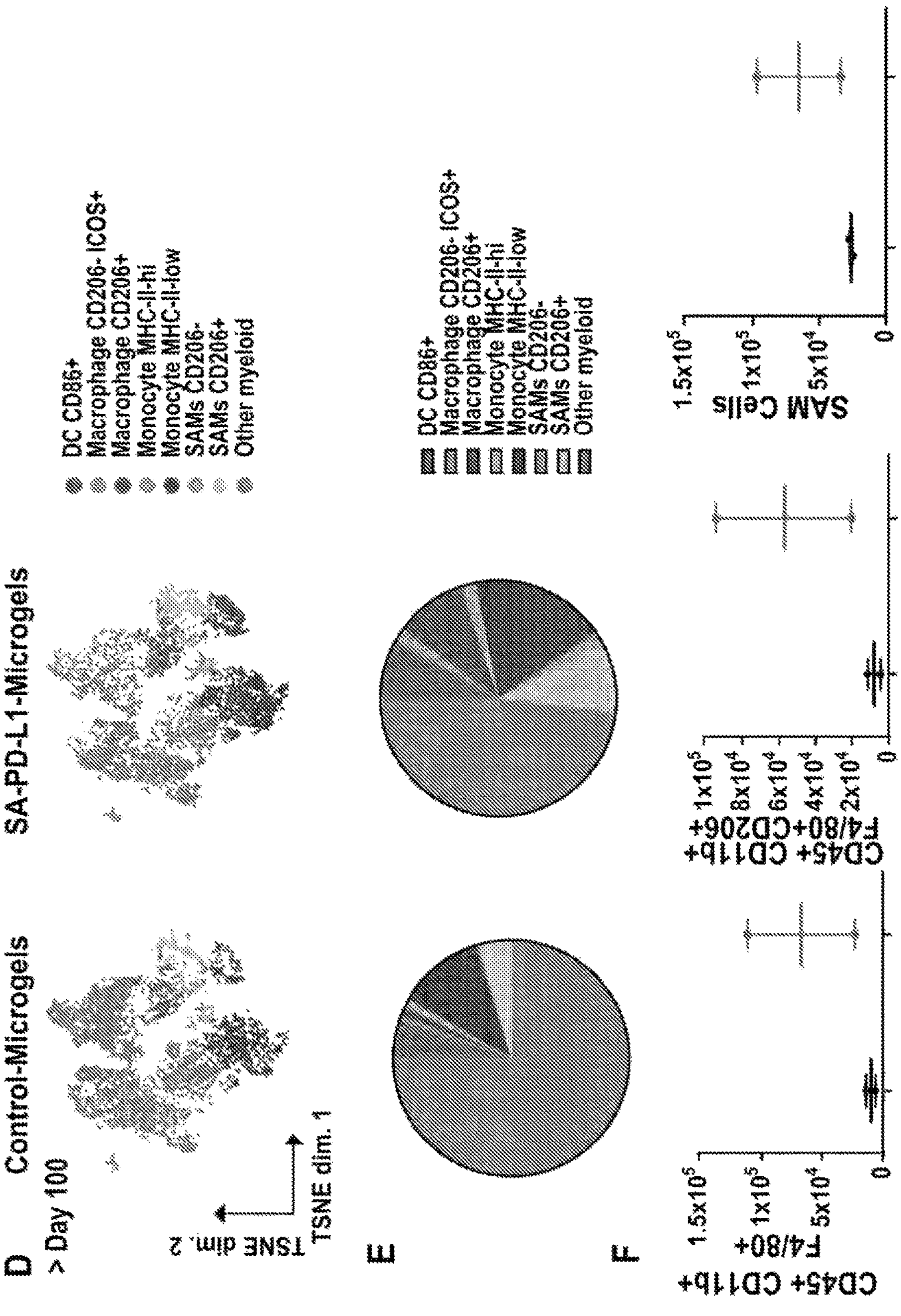
FIG. 13(D-F)

C

B

CROSSLINKED HYDROGEL FOR IMMUNE CHECKPOINT BLOCKADE DELIVERY

CROSS-REFERENCE TO RELATED APPLICATION

This application is a national stage application filed under 35 U.S.C. § 371 of PCT/US2021/040863, filed Jul. 8, 2021, which claims priority to and benefit of U.S. Provisional Application 63/049,185, filed Jul. 8, 2020, the contents of which are hereby incorporated in their entirely.

ACKNOWLEDGEMENT OF GOVERNMENT SUPPORT

This invention was made with government support under grant number R21EB020107 awarded by the National Institutes of Health. The government has certain rights in the invention.

FIELD OF THE INVENTION

The invention is directed to hydrogel materials for the controlled delivery of immunomodulating agents. The compositions are useful to improve long-term acceptance of allogenic islet grafts, and can be used to treat type 1 diabetes.

BACKGROUND

Pharmacological inhibition of immune responses via chronic systemic immunosuppression is currently the major clinically accepted strategy to prevent rejection of grafts from donors with different genotype backgrounds (i.e. allografts). Whereas major advancements have been made in improving post-operative immunosuppression regimens, the need for long-term administration of these pharmacological agents is still associated with serious side effects, including infections, malignancies, and cardiac and kidney toxicity. One promising cell therapy that has suffered from the requisite of chronic immunosuppression is clinical islet transplantation (CIT). Transplantation of allogeneic pancreatic islets has the potential to restore insulin production, improve glycemic control, and reduce complications in subjects with type 1 diabetes (T1D). Despite major improvements in immunosuppression regimens, most transplant recipients lose insulin independence by ~5 years post-transplantation. Moreover, in the context of the patient population most affected by this pathology (i.e. children and young adults), the need for chronic immunosuppression does not meet the clinical objective of benefit without major risk, rendering this therapy available only to a subset of patients with refractory hypoglycemia. Thus, novel therapeutic strategies that address the challenge of immune rejection in the absence of chronic immunosuppression are urgently needed.

Immune checkpoint blockade has emerged in the last decade as a powerful approach to control pathogenic immune responses. One of the most effective and durable immunotherapies currently in clinical use involves the programmed cell death-1 (PD-1) pathway. In oncology settings, blockade of the receptor PD-1 or its ligand PD-L1 can have potent effects in reinvigorating immunological responses to cancer cells. Importantly, the PD-1/PD-L1 axis plays a central role in regulating alloimmune responses in the transplantation setting. Experimental models of fully mismatched cardiac allografts have demonstrated a need for an intact PD-1/PD-L1 interaction, whereby blockade of PD-1 leads to exacerbated rejection times. Investigation into the functional significance of this pathway in less allogeneic models (single antigen mismatch) in PD-1 knockout mice, however, demonstrates that PD-L1 plays a critical role in the induction and maintenance of transplant tolerance through an additional binding partner B7-1. Thus, although targeting either receptor or ligand can provide inhibitory signals to immune cells, PD-L1 ligand delivery represents a more attractive approach for therapeutic delivery because (i) it can regulate immune responses in both lymphoid and nonlymphoid organs, (ii) has a unique role in promoting self-tolerance, and (iii) can signal through other receptors, in particular, B7-1 (same binding family as CTLA-4 receptor) which controls peripheral homeostasis of T regulatory cells.

Within the context of TID, the PD-1/PD-L1 axis is pivotal to autoimmunity, as seen by abnormalities in PD-L1 presentation in human patients with T1D and disease halting in transgenic models expressing PD-L1. Strategies aimed at employing PD-L1 to control disease progression and diabetes reversal have ranged from genetically modifying islets to express PD-L1 to improve graft survival in allogeneic transplantation models to the delivery of antigen-presenting-cells genetically or chemically modified to overexpress PD-L1. However, these approaches face barriers to clinical translation or rely on clinically relevant pharmacological interventions that lack evidence of longevity, limiting the long-term effect of the therapeutic strategy. Delivery of systemic forms of checkpoint inhibitors, such as PD-L1, can improve transplant outcomes. However, systemic delivery of these proteins has been associated with non-specific immune responses and high rates of immune-related toxicity.

There remains a need for improved methods of treating diabetes, including T1D. There remains a need for improved methods of delivering therapeutic agents, including therapeutic proteins, to patients in need thereof. There remains a need for improved methods of delivering checkpoint inhibitors with reduced immune related toxicity and non-specific immune responses.

SUMMARY

In accordance with the purposes of the disclosed materials and methods, as embodied and broadly described herein, the disclosed subject matter, in one aspect, relates to compounds, compositions and methods of making and using compounds and compositions. In specific examples, discloses are hydrogel compositions with surface presenting PD-L1. The compositions can be used to regulate alloimmune responses to pancreatic islets within a graft microenvironment. The compositions provide controlled delivery of PD-L1 within the graft, as a localized means of immune regulation, and can achieve sustained survival of allogeneic islet grafts. The compositions allow long-term survival of islet allografts in the absence of chronic systemic immunosuppression.

Described herein are PD-L1-engineered biomaterials wherein streptavidin-conjugated PD-L1 (SA-PD-L1)(such as, for example, SEQ ID NO: 2 and SEQ ID NO: 6) is displayed on a biocompatible material, such as a hydrogel, such as a polyethylene glycol (PEG) hydrogel, as well as methods of making and using such PD-L1-engineered biomaterials, such as for immunomodulation, such as for preventing or reducing the risks of rejection of cellular or tissue grafts and/or the treatment of T1D.

In accordance with some embodiments, there are provided biomaterial engineered to display PD-L1 moieties. In accordance with some embodiments, there are provided hydrogels engineered to display PD-L1 moieties. In accordance with some embodiments the hydrogel comprises a chimeric PD-L1 protein comprising a PD-L1 moiety and a streptavidin or avidin moiety conjugated via biotin to the hydrogel. In accordance with some embodiments, the hydrogel is a polyethylene glycol (PEG) microgel engineered to display a biotin moiety. In accordance with some embodiments, there are provided polyethylene glycol (PEG) hydrogels that display PD-L1 moieties. In specific embodiments, the hydrogels comprise biotin moieties conjugated to SA-PD-L1 moieties.

In accordance with any embodiments, the biomaterial may comprise an immunosuppressive drug, such as rapamycin. In some embodiments, the PD-L1-engineered hydrogels further comprise an immunosuppressive drug, such as rapamycin. In some embodiments, PD-L1-engineered biomaterials or hydrogels that further comprise an immunosuppressive drug provide controlled release of the drug.

In accordance with any embodiments, the biomaterial may comprise a graft cell, such as PBMCs, bone marrow cells, hematopoietic stem cells, stem cells, mesenchymal stem cells, dendritic cells, dendritic cells pulsed with autoantigens, human beta cell products, and splenocytes. In some embodiments the graft cell is encapsulated in the biomaterial.

In accordance with some embodiments, there are provided methods of effecting immunomodulation or inducing immune tolerance comprising administering to a subject in need thereof a PD-L1-engineered biomaterial or hydrogel as described herein. In some embodiments, the method comprises administering an amount of biomaterial effective to induce immune tolerance. In accordance with some embodiments, the administering is by transplantation.

In accordance with any embodiments, the subject may be a human, a non-human primate, a pig, a dog, a cat, a cow, a sheep, a horse, a rabbit, a mouse, or a rat.

In some embodiments, the subject is in need of immune tolerance to a graft cell, such as PBMCs, bone marrow cells, hematopoietic stem cells, stem cells, mesenchymal stem cells, dendritic cells, dendritic cells pulsed with autoantigens, human beta cell products, and splenocytes. In accordance with some embodiments, the method is for preventing or reducing the risks of rejection of cellular or tissue grafts and/or the treatment of T1D.

In accordance with any embodiments, the method may further comprise administering a graft cell, such as PBMCs, bone marrow cells, hematopoietic stem cells, stem cells, mesenchymal stem cells, dendritic cells, dendritic cells pulsed with autoantigens, human beta cell products, and splenocytes. In some embodiments, the biomaterial comprises the graft cell. In some embodiments the graft cell is encapsulated in the biomaterial.

In some embodiments, the subject is in need of treatment for T1D, and the method optionally further comprises administering pancreatic islet cells to the subject. In some embodiments, the subject is in need of treatment or prevention of allograft rejection, and the method optionally further comprises administering to the subject cells from an allograft donor. In some embodiments, the subject is in need of treatment or prevention of xenograft rejection, and the method optionally further comprises administering to the subject cells from a xenograft donor. In some embodiments, the xenograft donor is a human, a non-human primate, a pig, a dog, a cat, a cow, a sheep, a horse, a rabbit, a mouse, or a rat. In some embodiments, the subject is in need of treatment or prevention of autograft rejection, and the method optionally further comprises administering to the subject autologous graft cells. In some embodiments, the autologous graft cells are obtained by induced pluripotency. In some embodiments, the subject is in need of treatment or prevention of autoimmunity, and the method optionally further comprises administering to the subject autoantigen presented on a cell selected from (i) a cell expressing the autoantigen (ii) a cell decorated with the autoantigen and (iii) a dendritic cell pulsed with the autoantigen.

In accordance with some embodiments, there are provided methods of making biomaterials or hydrogels engineered to display PD-L1, comprising contacting a biotinylated biomaterial or hydrogel with SA-PD-L1 moieties.

In accordance with some embodiments, there are provided biomaterials engineered to display a PD-L1 protein as described herein, for inducing immune tolerance in a subject in need thereof.

In accordance with some embodiments, there are provided uses of biomaterials engineered to display a PD-L1 protein as described herein in the preparation of medicament for inducing immune tolerance in a subject in need thereof.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

The details of one or more embodiments are set forth in the descriptions below. Other features, objects, and advantages will be apparent from the description and from the claims.

BRIEF DESCRIPTION OF THE FIGURES

FIG. 1 depicts microfluidic flow-generated biotinylated microgels (hydrogel particles) allow controllable capturing of SA-modified proteins. (A) Transmission and orthogonal projection images of biotinylated microgels and SA-PD-L1, respectively; microgels were incubated in streptavidin-AlexaFluor488 (AF488) showing binding to microgels (green), SA-PD-L1 was immobilized on the biotinylated microgels and stained with and anti-PD-L1 antibody followed by secondary antibody staining. Scale bar 200 μm. (B) Microgels have an average size of 195 μm, CV ~6% and homogenous biotinylation as seen by labeling with streptavidin AF488. (C) Fluorescence intensity values and binding curve fits (lines) for biotin-4-fluorescein (B4F) competition assay showing equivalent binding behavior among SA-PD-L1 (blue), SA (red), and commercial streptavidin (black). (D, E) Microgels can efficiently capture SA-PD-L1 as seen by fluorescent intensity measurements of SA-PD-L1 labeled with AF488.

FIG. 2 depicts SA-PD-L1-presenting microgels do not impact islet viability and function. (A) Mitochondrial activity measured via MTT demonstrated no differences between islets cultured alone (blue circles) compared to islets co-culture with SA-PD-L1-presenting microgels (red squares). (B) Glucose-stimulated insulin secretion (GSIS) of murine islets indicate high cytocompatibility of microgel-protein platform. Inset: stimulation index (high over first low). (C) Live/dead z-projection confocal microscopy images of free and islets co-cultured with microgels (green=viable; red=dead). Scale bar 50 μm. (D) Profile of cytotoxic cytokines demonstrated no differences between free islets or islets co-culture with SA-PD-L1-presenting microgels for MIP-1α, IL-6, and MCP-1. (E) Syngeneic transplants of 600 IEQ with 1200 SA-PD-L1-presenting microgels did not affect engraftment and function (n=6 red circles, SA-PD-L1 microgels) compared to islets alone (n=3 blue squares, control). Graft removal at 40 days post-transplantation demonstrated normoglycemic reversal in a cohort of animals. (F) Graft potency at 30 days post-transplantation measured via an intraperitoneal glucose tolerance test (IPGTT) demonstrated no differences in SA-PD-L1-presenting microgel group compared to age-matched naïve animals (SA-PD-L1 microgels red solid lines; naïve, dashed blue lines). Inset: calculated area under the curve. (G) Immunohistochemistry of grafts stained for insulin (green), glucagon (red), and nuclear staining (blue). Scale bar 50 μm. In vitro cytocompatibility data was collected from 2 independent islet isolation experiments, with representative data presented as the mean±S.D. of group replicates (n=3 biological independent samples for each group). Data was analyzed using Student's t-test with Welch's correction.

FIG. 3 depicts delivery of SA-PD-L1 via microgels increases retention in transplant microenvironment in vivo. (A) Fluorescence images of animals transplanted with near-infrared dye-labeled free protein (free SA-PD-L1) or SA-PD-L1 tethered to microgels. Normalized scale bar to radiant efficiency. (B) Quantification of in vivo fluorescence radiant efficiency, mean±SD for free SA-PD-L1 (n=5) or SA-PD-L1-presenting microgels (n=4). Traces were fit with a non-linear regression model (solid lines). Mix effects model, *$p<0.05$,  $P<0.005$, *$p<0.0005$.

FIG. 4 depicts SA-PD-L1-presenting microgels improve long-term function of islet allografts. (A) Graphical depiction of transplant strategy. Islets and microgels (1 IEQ BALB/c islets: 2 microgels) were transplanted in the EFP of diabetic allogeneic C57BL/6 mice; with or without a short course of rapamycin (RAPA, 0.2 mg/kg daily for 15 days). (B) Blood glucose levels (shadowed area represents S.E. for each group) and (C) graft survival rate of diabetic recipients. Controls received biotinylated microgels without RAPA, n=5 (green); SA-PD-L1 free+RAPA, n=6 (magenta); SA-PD-L1-microgels without RAPA, n=9 (blue); control biotinylated microgels under a short RAPA treatment, n=14 (black lines); SA-PD-L1-microgels under short RAPA treatment, n=12 (SA-PD-L1+RAPA, red lines). (D) Intraperitoneal glucose tolerance test (IPGTT) showed no differences between SA-PD-L1-microgel+RAPA group (red solid line, shadowed area represents S.E.) and age-matched naïve (dashed grey line) mice, whereas 4/5 control+RAPA animals were unable to regulate blood glucose within 120 min post-glucose bolus administration. Inset: calculated area under the curve. (E) Immunostaining of tissue sections from animals at 35-40 days post-transplantation. Samples were stained for insulin (red) and DNA (DAPI, blue). Scale bar 50 μm. (F) SA-PD-L1-microgels+RAPA leads to FoxP3+ T cell recruitment to the local graft microenvironment. Staining of tissue sections from animals at 35-40 days post-transplantation. Samples were stained for FoxP3 (green), CD3 (red) and DNA (DAPI, blue). Scale bar 100 μm. Bonferroni-corrected survival curves were analyzed using Mantel-Cox test ($\chi^2=8.4$, df=1 for SA-PD-L1-microgels+RAPA vs control+RAPA). ANOVA with Tukey's multiple comparisons test was used to analyze AUC.

FIG. 5 depicts SA-PD-L1-presenting microgels result in regulatory immune responses in the local graft microenvironment early post-transplant. (A) Graphical representation of the experimental setup. (B) Heatmap presenting fold change in gene expression in animals receiving alloislets and SA-PD-L1-presenting microgels compared (red filled) to mice receiving islets and control microgels (open) (n=3 mice per group, run in triplicates each). Yellow represents fold change >5. (C) tSNE plots to visualize CD45 CD3+ cells infiltrating cells to the EFP for naïve, control-microgel+RAPA (n=3) and SA-PD-L1-microgels+RAPA (n=4) animals at day 3 post-transplantation. (D) Pie chart distribution of the cell populations observed after high dimensional clustering after 3 days. (E) tSNE and (F) pie chart distribution used to visualize CD45 CD3+ cells infiltrating cells to the epidydimal fat pad for naïve, control-microgel+RAPA (n=4) and SA-PD-L1-microgels+RAPA (n=4) animals at day 14 post-transplantation. (G) Kinetics of CD4+(solid lines) and CD8+ cells (dashed lines) post-transplantation; naïve animals are represented in gray, control-microgel+RAPA in black and SA-PD-L1-microgels+RAPA in red. (H) CD4:CD8 ratio at 3 and 14 days post-transplantation. (I-J) Absolute cell number of FoxP3 expressing cells in the CD4 and CD8 compartment of animals receiving the biomaterial with or without SA-PD-L1 at 3 and 14 days post-transplantation. (K-L) Absolute number of cells expressing exhaustion markers (PD1, Tim3, Lag3) at day 14 post-transplantation. Student's t-test with Welch's correction was used to analyze gene replicates. Two-way ANOVA with multiple comparisons Bonferroni corrected was used to analyze absolute cell counts for data in (H), (I), (J). Student's t-test was used to analyze data in (K), and (L). Panel A was created with BioRender.com.

FIG. 6 depicts SA-PD-L1-presenting microgels results modulate myeloid cell recruitment to the local graft microenvironment early post-transplant. (A) tSNE plots were used to visualize CD45+CD11b+ cells infiltrating cells to the EFP for naïve, control-microgel+RAPA (n=3) and SA-PD-L1-microgels+RAPA (n=4) animals at day 3 post-transplantation. (B) Pie chart distribution of the cell populations observed after high dimensional clustering after 3 days. (C) tSNE and (D) pie chart distribution were used to visualize CD45+CD11b+ cells infiltrating cells to the epidydimal fat pad for naïve, control-microgel+RAPA (n=4) and SA-PD-L1-microgels+RAPA (n=4) animals at day 14 post-transplantation. (E) Absolute cell number of CD45+CD11b+ expressing cells in animals receiving the biomaterial with (red lines) or without SA-PD-L1 (black lines) at 3 and 14 days post-transplantation. (F) Absolute cell number of CD45+CD11b+F4/80+ expressing cells in animals receiving microgels with (red lines) or without SA-PD-L1 (black lines) at 3 and 14 days post-transplantation. (G-H) Kinetics of CD45+CD11b+F4/80+CD206+ and SAM (CD11b+F4/80+CD11c+/−CD206hiCD86+MHCII+) cells in grafts at 3 and 14 days post-transplantation. Two-way ANOVA with multiple comparisons Bonferroni corrected was used to analyze absolute cell counts for data in (E) and (F).

FIG. 7 depicts biotinylated microgels efficiently capture SA-PD-L1. (A) Standard curve of SA-PD-L1 labeled with AlexaFluor488 used to calculate capturing efficiency in FIG. 1F. Data mean±SEM (n=4). (B) Western blot of SA-PD-L1 protein as a control, and supernatant post-conjugation to biotinylated microgels. (C) Confocal image of SA-PD-L1-presenting and biotinylated control microgels incubated with an AF488-conjugated anti-PD-L1 antibody, demonstrating immobilization of the surface of the biotinylated microgels, microgels not exposed to SA-PD-L1 were used as controls. Scale bar 200 μm. (D) Image of microgels conjugated with AF488-labeled SA-PD-L1. Scale bar 200 μm.

FIG. 8 depicts SA-PD-L1 promotes iTreg and a suppressive phenotype in vitro. (A) Development of FoxP3+iT reg cells was assessed by flow cytometric analysis of CD25/FoxP3 expression after co-culture of naive $CD4^+CD62L^+$ $CD25^-$ T cells with anti-CD3 and anti-CD28 and the absence/presence of TGFβ (2 ng/mL), IL-2 (20 U/mL), and 25 μg/mL of soluble SA-PD-L1 in solution for 3 d. Data represent mean±S.D. (B) SA-PD-L1 function was assessed by $[^3H]$thymidine incorporation in a mixed lymphocyte reaction of splenocytes of 4 C mice and irradiated BALB/C splenocytes (1:8 ratio). Data was collected after 3 d in culture. For iTreg conversion assay, data was collected from 3 independent experiments and is represented as the mean±S.D. of the replicates. For the suppression assay, data was collected from 2 independent experiments, with representative data presented as the mean±S.D. of group replicates (n=3 independent biological samples for each group). ANOVA with Tukey's multiple comparisons test was used to analyze data. Panel A and B were created with BioRender.com.

FIG. 9 depicts co-culture of islets with SA-PD-L1 microgels does not affect function or engraftment of islets. (A) Immunostaining of cultured islets for insulin (yellow), nuclear staining (DAPI), and glucagon (magenta). Insulin and glucagon positive cells were observed in both islets culture alone or together with SA-PD-L1-presenting microgels. Scale bar 50 μm. (B) Histological analysis of syngeneic grafts shows engraftment and re-vascularization of islets co-transplanted with SA-PD-L1-presenting microgels in the EFP of STZ-diabetic C57BL/6 mice. Scale bars 100 μm left, and 50 μm right. (C) Immunostaining of tissue sections at 30 days post-transplantation, staining on different areas in the tissue are shown. Samples were stained for insulin (red), CD31 (green) and nuclear staining (DAPI, blue). Top row shows an area with a large cross-section of a blood vessel to demonstrate the efficiency of CD31 staining; bottom image refers to graft area demonstrating robust insulin staining and CD31 vessels within the graft. Scale bar 20 μm.

FIG. 10 depicts blood glucose traces of individual animals. Readings were taken on STZ-diabetic C57BL/6 mice transplanted with BALB/c islets and the following: (A) microgels alone (green, n=5); (B) control-microgels+RAPA (black, n=14); (C) free protein delivered locally to the graft site with RAPA (magenta, n=6); (D) SA-PD-L1-microgels without RAPA (blue, n=9); (E) SA-microgels with RAPA (orange, n=7); (F) SA-PD-L1-microgels+RAPA (red, n=12); (G) naïve animals (light grey, n=7); (H) diabetic control animals (dark grey, n=9). (I) Total insulin levels after terminal pancreatectomy to evaluate residual insulin function in transplanted animals compared to naïve and diabetic controls. (J-K) Mixed lymphocyte reaction for self- and allo-reactivity. Normalized response showing fold activation for CD4 and CD8 cells exposed to BALB/c alloantigens over the same animal's response to self-antigen after co-culture for 4 days.

FIG. 11 depicts histological evaluation of alloislet grafts. (A) Staining of tissue sections from animals at 35-40 days post-transplantation as isotype controls. Samples were stained for insulin (red), FoxP3 (green), CD3 (red), and DNA (DAPI, blue). Scale bar 100 μm. (B) H&E and trichrome staining of grafts of control-microgels+RAPA (30 days post-transplant), SA-PD-L1-microgels+RAPA (100 days post-transplant), and SA-PD-L1-microgels no RAPA (60 days post-transplant. (C) H&E images of islets from SA-PD-L1 microgels+RAPA that rejected (left) or did not reject the graft (right). Scale bar 100 μm.

FIG. 12 depicts SA-PD-L1-presenting microgels have no adverse events. (A) Hematoxylin and eosin-stained section of liver, kidney, lung, and spleen tissue of animals receiving either control microgels or SA-PD-L1-presenting microgels at 50-70 days post-transplantation. Staining patterns are consistent for 12 independent biological samples. Scale bar 100 μm. (B) Serum levels of enzymes aspartate transaminase (AST) and (C) alanine aminotransferase (ALT) for mice receiving microgels alone or SA-PD-L1-conjugated microgels after 50-70 days post-transplantation. (D-F) Dot blot images to examine for presence of antibodies in allograft recipient serum pre-transplantation, 3 weeks, and 12 weeks post-transplantation. ImageJ analysis of dot blot pixels performed by protein array analyzer tool. (G-I) Quantification of the frequency of positive antibodies (determined as a pixel intensity >5 fold over background). Serum was tested against commercial streptavidin (commercial SA); SA (SA); chimeric PD-L1 (SA-PD-L1); and mouse IgG as an internal control (IgG Control). No differences in the presence of antibodies for SA were observed between the control microgel or the SA-PD-L1 microgel group pre- and post-transplantation for the commercial or the SA alone. A significant increase in positive reactions against SA-PD-L1 was observed in the SA-PD-L1-microgel group compared to control at 3 weeks post-transplant (p=0.03), but no antibodies were detected at 12 weeks post-transplantation.

FIG. 13 depicts immune cell profile of non-rejecting grafts at >100 days post-transplantation. (A) tSNE plots and (B) cluster cell distribution for CD45+CD3+ cells in the grafts of control-microgel+RAPA (n=2) and SA-PD-L1-microgels+RAPA (n=2) animals. (C) Absolute cell counts for CD4:CD8 and regulatory cell ratios in the grafts. (D) tSNE plots and (E) cluster cell distribution for CD45+CD11b+ cells in the grafts of control-microgel+RAPA (n=2) and SA-PD-L1-microgels+RAPA (n=2) animals. (F) Absolute number of CD45+CD11b+F4/80+, CD45+CD11b+F4/80+CD206+, and SAMs expressing cells in the EFP of animals.

DETAILED DESCRIPTION

Figure 14A:
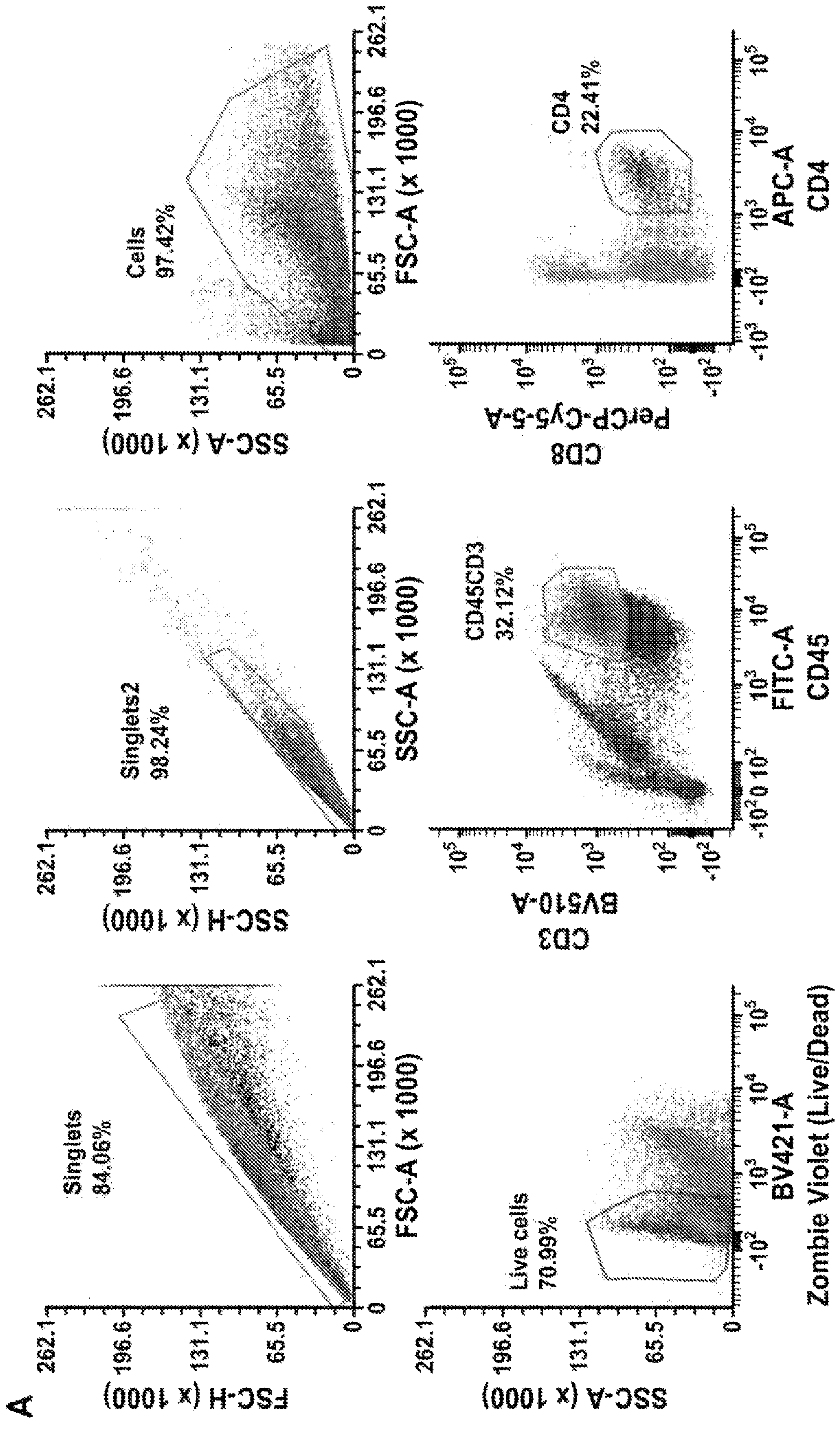
FIG. 14 depicts gating strategy for CD45+CD3+ cell analysis. (A) Singlets and cells were gated based on the FSS vs SSC scatter. Live cells were gated based on expressing a fixable live/dead dye. CD45+CD3+ positive cells were gated for every sample. This gate was exported to the CATALYST pipeline for high dimensional analysis. (B) FCS files from all clusters were exported from CATALYST and plotted in FCS Express, and compared against FMOs or isotype for marker expression. (C) Heatmap of marker clustering and cluster id used for tSNE representation.
Figure 14B:
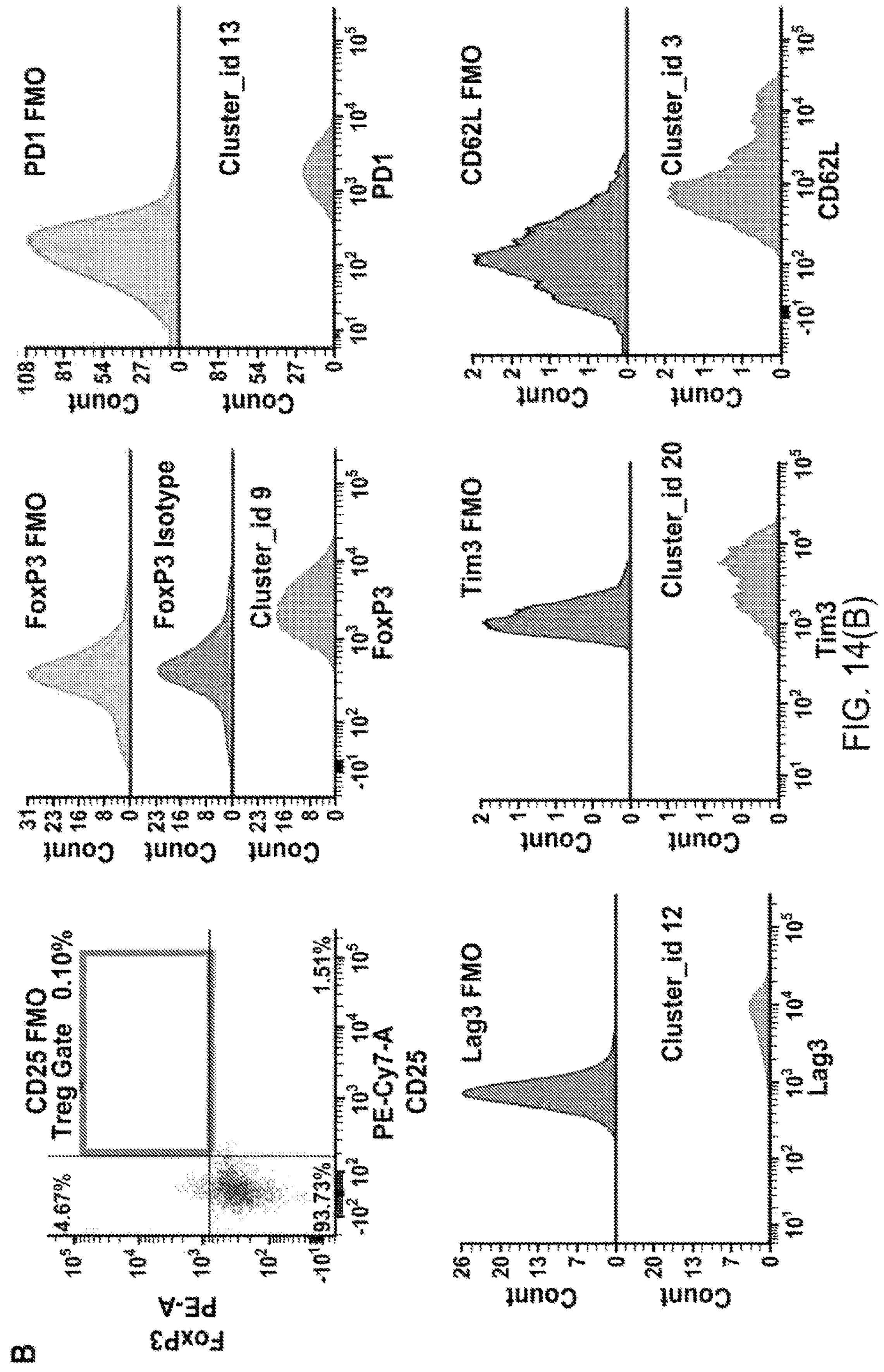
Figure 14C:
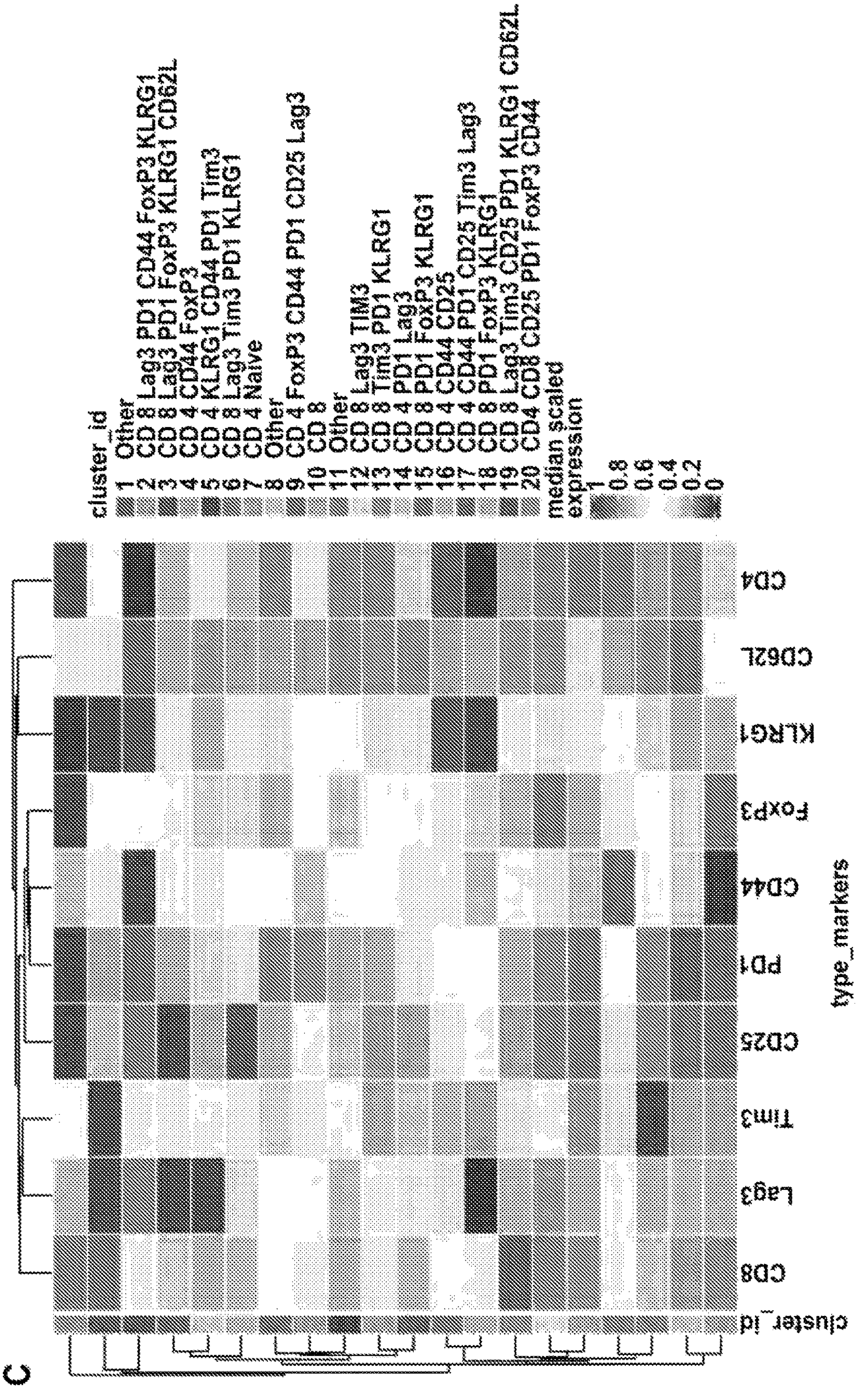
Figure 15A:
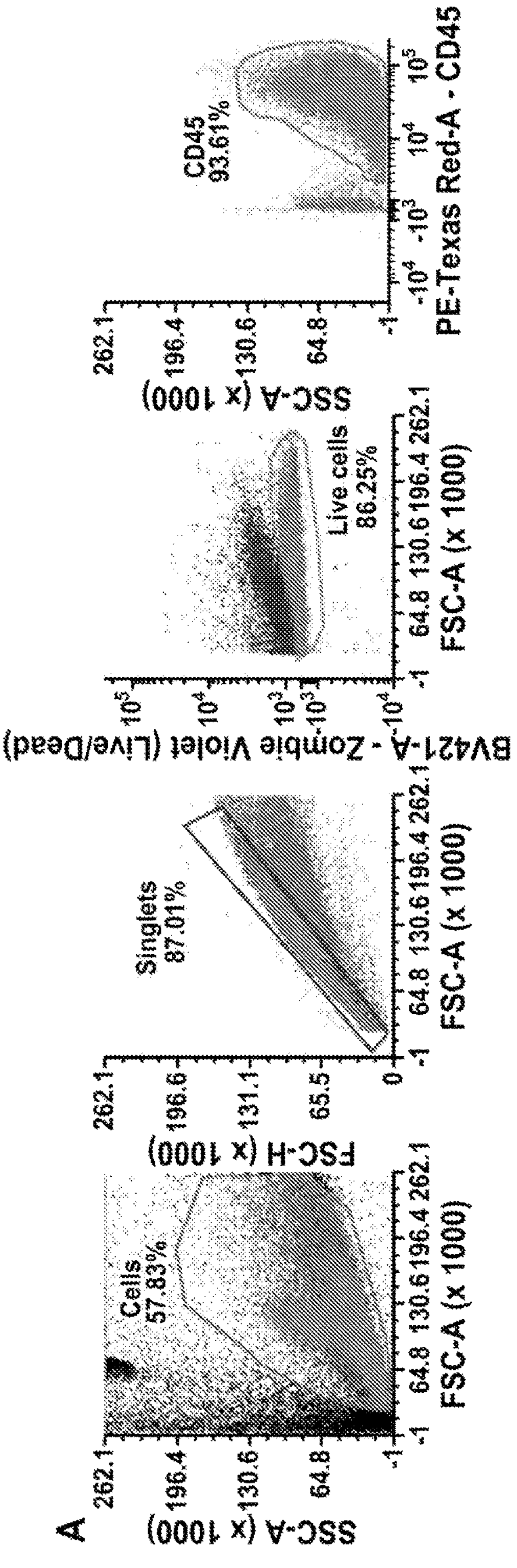
FIG. 15 depicts gating strategy for CD45+ cell analysis. (A) Singlets and cells were gated based on the FSS vs SSC scatter. Live cells were gated based on expressing a fixable live/dead dye. CD45+ positive cells were gated for every sample. This gate was exported to the CATALYST pipeline for high dimensional analysis. (B) FCS files from all clusters were exported from CATALYST and plotted in FCS express, and compared against FMOs or isotype for marker expression. (C) Heatmap of marker clustering and cluster id used for tSNE representation.
Figure 15B:
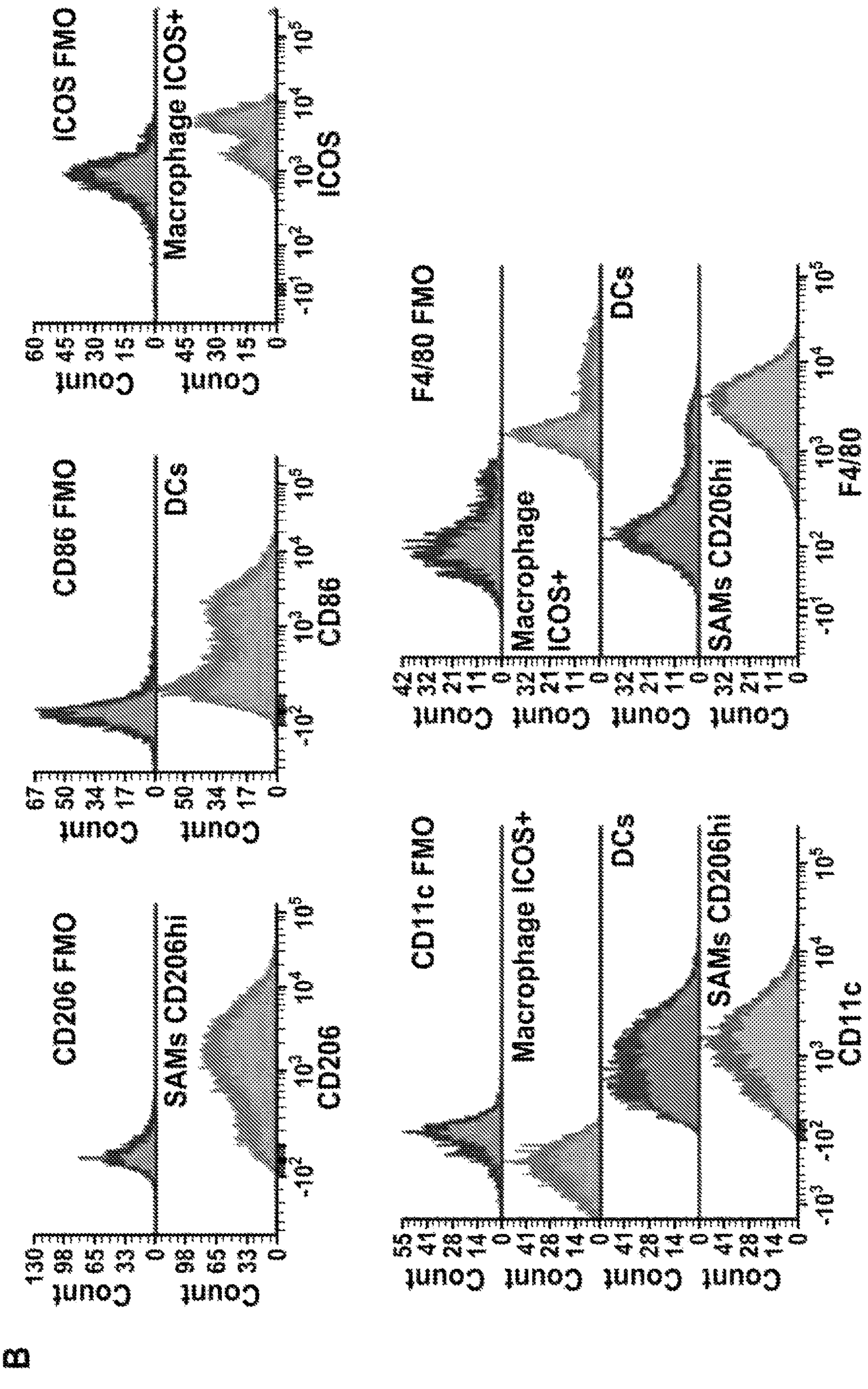
Figure 15C:
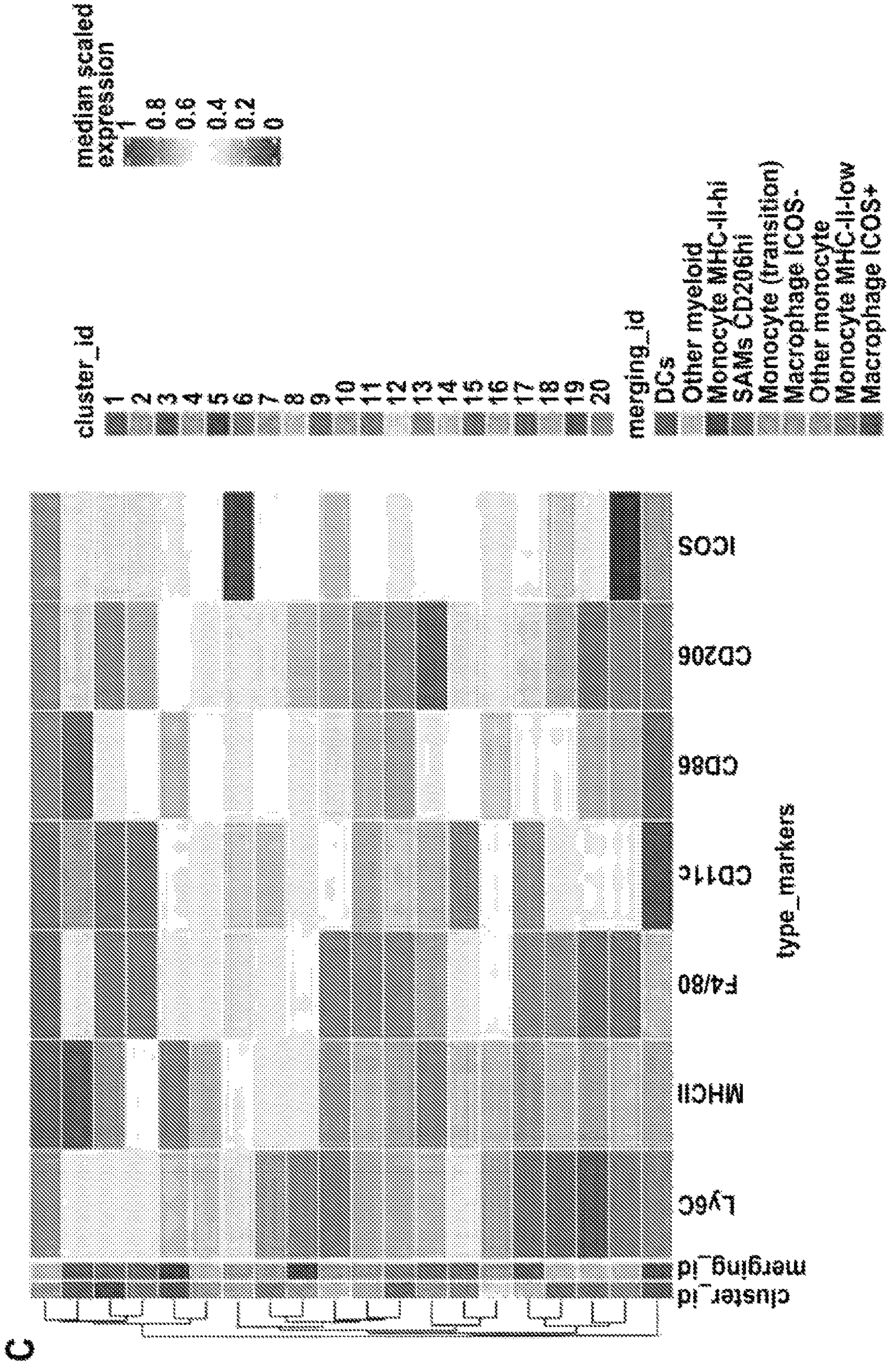

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

As used herein "biotin" includes biotin-containing moieties that are able to bind to surfaces, such as cell surfaces, such as NHS-biotin and EZ-Link™ Sulfo-NHS-LC-Biotin (Pierce). Biotin and protein-reactive forms of biotin are available commercially.

SA or avidin fragments which retain substantial binding activity for biotin, such as at least 50% or more of the binding affinity of native SA or avidin, respectively, also may be used. Such fragments include "core streptavidin" ("CSA"), a truncated version of the full-length streptavidin polypeptide which may include streptavidin residues 13-138, 14-138, 13-139 or 14-139. See, e.g., Pahler et al., J Biol. Chem., 262: 13933-37 (1987). Other truncated forms of streptavidin and avidin that retain strong binding to biotin also may be used. See, e.g. Sano et al., J Blot Chem. 270(47): 28204-09 (1995) (describing core streptavidin variants 16-133 and 14-138) (U.S. Pat. No. 6,022,951). Mutants of streptavidin and core forms of strepavidin which retain substantial biotin binding activity or increased biotin binding activity also may be used. See, e.g., Chilkoti et al., Proc Natl Acad Sci, 92(5): 1754-58 (1995), Reznik et al., Nat Biotechnol, 14(8): 1007-11(1996). For example, mutants with reduced immunogenicity, such as mutants mutated by site-directed mutagenesis to remove potential T cell epitopes or lymphocyte epitopes, can be used. See Meyer et al., Protein Sci., 10: 491-503 (2001). Likewise, mutants of avidin and core forms of avidin which retain substantial biotin binding activity or increased biotin binding activity also may be used. See Hiller et al., J Biochem, 278: 573-85 (1991); and Livnah et al., Proc Natl Acad Sci USA 90: 5076-80 (1993). For convenience, in the discussion herein, the terms "avidin" and "streptavidin" (or "SA") encompass fragments, mutants and core forms of these molecules.

Avidin and streptavidin are available from commercial suppliers. Moreover, the nucleic acid sequences encoding streptavidin and avidin and the streptavidin and avidin amino acid sequences are known. See, e.g., GenBank Accession Nos. X65082; X03591; NM 205320; X05343; Z21611; and Z21554.

The synthetic hydrogels disclosed herein have a three-dimensional network structure containing a network of crosslinked hydrophilic polymers. The three-dimensional structure may be in the form of particles, and can have an average diameter from 10-1,000 μm, from 25-1,000 μm, from 50-1,000 μm, from 100-1,000 μm, from 10-500 μm, from 25-500 μm from 50-500 μm, from 100-500 μm, from 10-250 μm, from 25-250 μm from 50-250 μm, from 100-250 μm, from 100-200 μm, from 150-250 μm, from 150-200 μm, or from 200-250 μm. Average particle diameter may be determined using conventional imaging and data processing.

Hydrophilic polymers useful in the three-dimensional network structures include polyalkylene glycol polymers, polyalkylene oxide homopolymers such as polypropylene glycols, polyoxyethylenated polyols, copolymers thereof and block copolymers thereof, as well as poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. The molecular weight of the hydrophilic polymer (prior to crosslinking) can be from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

In certain embodiments, the crosslinked hydrophilic polymer is a polyethylene glycol, i.e., PEG. The PEG can have a molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, from 40,000-60,000, from 1,000-10,000, from 1,000-7,500, from 2,500-7,500, or from 5,000-25,000.

In preferred embodiments, the crosslinked hydrophilic polymer is a branched or multi-arm hydrophilic polymer. As used herein, a multi-arm polymer describes a polymer having a central core with at least two polymers covalently attached thereto. Multi-arm polymers can have 2, 3, 4, 5, 6, 7, 8 or more polymer arms. Preferred multi-arm polymers, as defined above, include those with 4 arms. Generally, all of the polymers attached to the core are the same, but in some instances different hydrophilic polymers, as defined above, can be used. Suitable cores include those derived from polyols, including glycerol (3-arm), pentaerythritol (4-arm), tetraglycerol (6-arm), and hexaglycerol (8-arm). A particularly preferred polymer is a 4-arm PEG, having a total molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000.

The hydrogel compositions disclosed herein include biotin residues extending from the surface of the composition. The biotin residue may be conjugated to a hydrophilic, linear polymer which is covalently incorporated into the three-dimensional network structure. Hydrophilic polymers useful for conjugating biotin residues include polyalkylene glycol polymers, polyalkylene oxide homopolymers such as polypropylene glycols, polyoxyethylenated polyols, copolymers thereof and block copolymers thereof, as well as poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. In certain embodiments, a polyethylene glycol is the hydrophilic polymer used to conjugate biotin to the three-dimensional network. The molecular weight of the hydrophilic polymer can be from 1,000-25,000, from 1,000-15,000, from 1,000-10,000, from 1,000-5,000, from 1,000-2,500, from 500-25,000, from 500-15,000, from 500-10,000, from 500-5,000, from 500-2,500, from 500-1,500, from 750-1,250, or from 500-1,000.

Suitable core groups can be derived from a polyol such as glycerol, pentaerythritol, sorbitol, mannitol, tetraglycerol, and hexaglycerol. In some instances, the core can have the general structure:

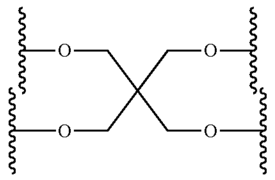

or

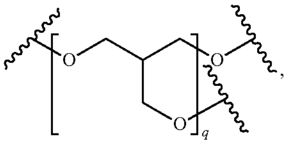

, wherein q is any integer, for instance 1, 2, 3, 4, 5, 6, 7, 8, 9, or 10 and ⌇ represents a link to a hydrophilic polymer, as described above. Other suitable polyols include carbohydrates, including monosaccharides and di-saccharides, such as glucose, xylose, mannose, galactose, sucrose, maltose, trehalose and fructose, and cyclic polyols like cyclopropane-1,2,3-triol, cyclobutane-1,2,3,4-tetraol, cyclopentane-1,2,3,4-tetraol, cyclopentane-1,2,3,4,5-pentaol, cyclohexane-1,2,4,5-tetraol, cyclohexane-1,2,3,4,5,6-hexanol, and the like.

In certain embodiments, the crosslinked network has the general formula:

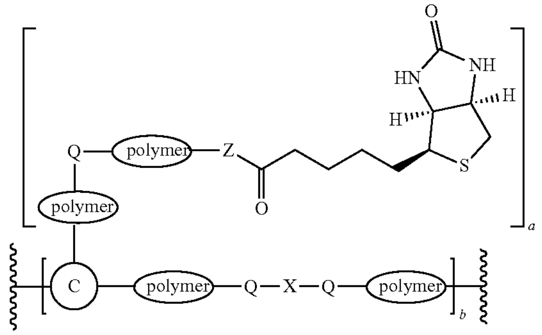

wherein 'polymer' in each case independently represents any hydrophilic polymer, including those defined above, the encircled C represents a core, Q represents a linker, X represents a crosslinker, Z is null or a linker, and the sum of a+b is from 3-10, from 3-8, from 3-6, from 3-5, 3, 4, 5, 6, 7, or 8.

In some embodiments, the hydrophilic polymer can be a poly(ethylene glycol), i.e., networks having the formula:

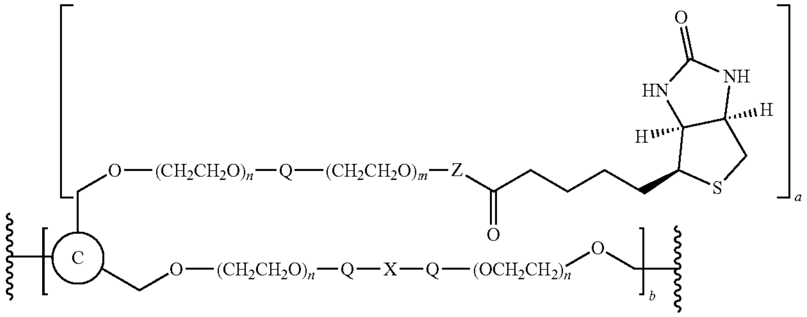

wherein encircled C, Q, X, Z, a, and b are as defined above, and each of n and m is independently selected from an integer from 10-50,000. In some instances, each n is in each case an integer from 15-30,000, from 15-15,000, from 15-7,5000, from 15-5,000, from 15-2,500, from 15-1,500, from 15-500, from 50-1,000, from 100-1,000, from 50-500, from 50-250, or from 50-150. In some instances, each m is an integer from 10-1,000, from 10-750, from 10-500, from 10-250, from 10-100, from 10-50, or from 10-25. In some embodiments, each $-(CH_2CH_2O)_n-$ unit can have an average molecular weight from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, from 40,000-60,000, from 1,000-10,000, from 1,000-7,500, from 1,000-5,000, from 2,500-7,500, or from 5,000-25,000. In some embodiments, each $-(CH_2CH_2O)_m-$ unit can have an average molecular weight from 250-50,000, from 250-25,000, from 250-10,000, from 250-5,000, from 250-2,500, from 500-2,500, from 500-1,500, or from 750-1,250.

Suitable Q group include those formed via Michael addition between a nucleophilic group on a hydrophilic polymer or crosslinker, and a Michael acceptor bonded to the hydrophilic polymer. For instance, in some embodiments, Q represents a group having the formula:

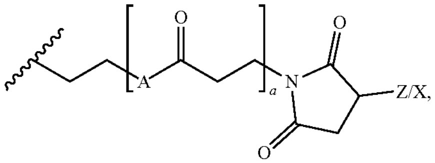

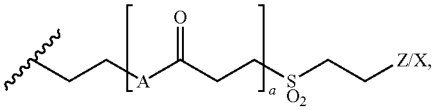

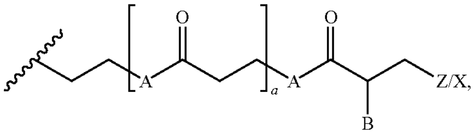 or

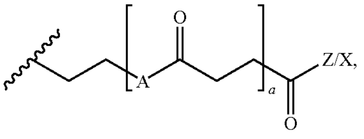

wherein A is independently selected from O or NH, a is independently selected from 0 or 1, B is selected from hydrogen or methyl, Z and X are as defined above, and ⌇ represents a link to a hydrophilic polymer, as described above.

The three-dimensional hydrogels may be prepared by reacting a compound of Formula (1):

[Formula (1)]

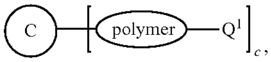

wherein encircled C and polymer are as defined above, $Q^1$ comprises an electrophilic group, and c is the sum of a+b, wherein a and b are as defined above, with a compound of Formula (2):

[Formula (2)]

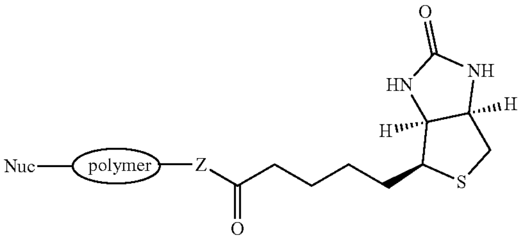

wherein polymer and Z are as defined above, and 'Nuc' is a nucleophilic group capable of reacting the $Q^1$ to give a compound of Formula (3):

[Formula (3)]

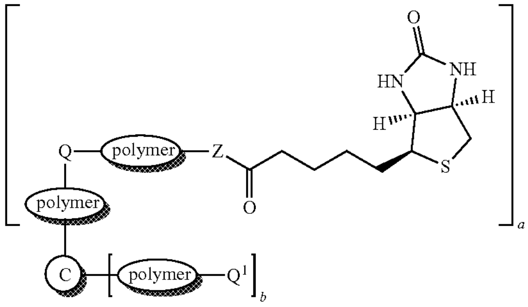

Preferred nucleophilic groups include SH and $NH_2$. The molar ratio of the compound of Formula (1) to the compound of Formula (2) is from 10:1 to 1:10, from 10:1 to 1:1, from 10:1 to 5:1, from 7.5:1 to 2.5:1, from 5:1 to 1:1, from 5:1 to 2.5:1, from or from 2.5:1 to 1.

The resulting product maybe crosslinked by reaction with a crosslinker compound having at least two nucleophilic groups, e.g., two thiol groups or two amino groups. In some embodiments, the crosslinker compound has the formula:

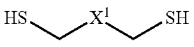 or 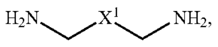

wherein $X^1$ is a $C_{1-8}$alkylene group, optionally substituted one or more times by OH, or $X^1$ is a poly(ethylene)glycol group, having from 1 to 20 monomer units. In preferred embodiments, $X^1$ is a group having the formula:

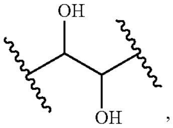,

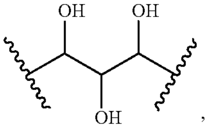, or

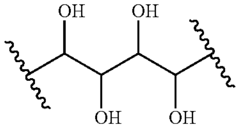

Preferred $Q^1$ groups include:

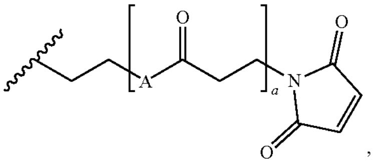

,

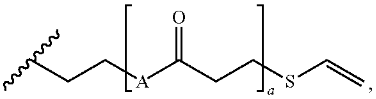

,

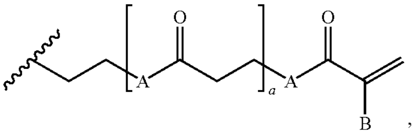

, or

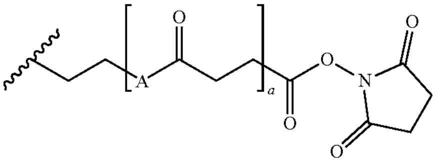

, wherein A is independently selected from O or NH, a is independently selected from 0 or 1, B is selected from hydrogen or methyl, and ⌇ represents a link to a hydrophilic polymer, as described above.

The resulting three dimensional hydrogel network may sized using a flow focusing microfluidic device to give microgels with the desired particle size (for example, approximately 200 μm). The microgels can be conjugated to SA-PD-L1 (the SA-PD-L1 comprising a mouse PD-L1 (such as, for example, a mouse PD-L1 as set forth in SEQ ID NO: 3 or a human Pd-L1 as set forth in SEQ ID NO: 7) conjugated to streptavidin (such as, for example SEQ ID NO: 4) including, but not limited to, a mouse SA-PD-L1 (SEQ ID NO: 2) or a human SA-PD-L1 (SEQ ID NO: 6) with or without a his-tag or any intervening linker sequence) by incubating the protein and microgels together for 0.5-10 hours at a temperature from 15-40° C., from 20-37° C., from 23-37° C., from 20-30° C., or from 20-27° C. 1 μg of SA-PD-1 may be combined with between 100-100,000 microgel beads, between 100-50,000 microgel beads, between 100-25,000 microgel beads, between 100-10,000 microgel beads, between 100-5,000 microgel beads, between 100-1,000 microgel beads, between 500-2,500 microgel beads, or between 500-1,500 microgel beads. In some embodiments, 1,000 particles of the hydrogel network are incubated with a solution comprising between 0.1-50 μg SA-PD-L1, between 0.1-25 μg SA-PD-L1, between 0.1-10 μg SA-PD-L1, between 0.1-5 μg SA-PD-L1, between 0.5-5 μg SA-PD-L1, or between 0.5-2.5 μg SA-PD-L1.

In some embodiments the biomaterial comprises or is formulated with (e.g., admixed with or blended with) an additional therapeutic agent, such as an immunosuppressant. Examples of suitable immunosuppressive drugs include rapamycin, cyclophosamide busulfan, fludarabine, methotrexate, sulfasalazine, hydroxychloroquine, azathioprine, tocilizumab, etanercept, adalimumab, anakinra, abatacept, rituximab, certolizumab, golimumab, cyclosporine, dexamethasone, methylprednisolone, prednisone, tacrolimus and triamcinolone. In some embodiments, the immunosuppressive drug is rapamycin.

In accordance with some embodiments, there are provided methods of effecting immunomodulation comprising administering to a subject in need thereof a PD-L1-engineered biomaterial as described herein. In accordance with some embodiments, the method is for preventing or reducing the risks of rejection of cellular or tissue grafts and/or the treatment of Type I diabetes.

In accordance with some embodiments, there are provided methods of inducing immunosuppression in a subject in need thereof comprising administering to the subject a PD-L1 biomaterial in an amount effective to induce immune tolerance. For example, administering a PD-L1 biomaterial along with a graft (e.g., a graft cell) may induce specific immune tolerance to the graft cell. Thus, in accordance with some embodiments, there are provided methods of inducing specific immune tolerance in a subject in need thereof comprising administering to the subject a graft cell PD-L1 biomaterial in an amount effective to induce immune tolerance to the graft cell.

As used herein "graft cell" refers to a donor cell (or tissue or organ comprising a cell), that is administered to a subject in need thereof. Types of graft cells include islet cells (e.g., pancreatic islet cells), splenocytes, PBMCs, bone marrow cells, mesenchymal stem cells, hematopoietic stem cells, stem cells, induced pluripotent stem cells, human beta cell products, hepatocytes, dendritic cells, macrophages, endothelial cells, cardiac myocytes, and vascular cells, and immune cells, including T cells, etc., depending on the condition being treated. In accordance with these methods the PD-L1 hydrogel induces specific immune tolerance to the graft cells.

To illustrate, a subject may be administered pancreatic islet cells to treat diabetes. In accordance with the methods described herein, the subject may be administered pancreatic islet cells and a hydrogel engineered to display PD-L1 (a "PD-L1 hydrogel") in order to specific induce immune tolerance to the pancreatic islet cells. In another example, the subject may be administered hepatocytes to treat acute liver failure or liver-based metabolic disorders. In accordance with the methods described herein, the subject may be administered hepatocytes and a PD-L1 hydrogel in order to induce immune tolerance to the hepatocytes.

In any embodiments, the graft cell may be administered as a preparation of isolated cells or as part of a tissue or organ.

In some embodiment, the graft cell is allogenic. In some embodiments, the graft cell is xenogenic. In some embodiment, the graft cell is from a human, a non-human primate, a dog, a cat, a cow, a sheep, a horse, a rabbit, a mouse, or a rat.

In some embodiment, the graft cell is autologous or autogenic (from the subject being treated). For example, an autologous graft cell may be derived from autologous tissue by induced pluripotency and differentiation of the induced pluripotent cells to the desired autologous graft cell. In some embodiments, cells from the subject are used to induce immune tolerance to self that has been interrupted in autoimmune disease. Exemplary cells suitable for use in these embodiments include mobilized hematopoietic stem cells, PBMCs, dendritic cells, and the like. In some embodiments, the cells are chosen from those that naturally express self antigens that are targeted in the autoimmune disease. For example, type I diabetes is an autoimmune disease wherein the body reacts and rejects pancreatic islet (β) cells. In early stages of diabetes, before all islet cells are rejected, it can be possible to induce tolerance to islet cells and thereby prevent the progression of diabetes.

Thus, in some embodiments, the subject is in need of immune tolerance to a graft cell, and a method of inducing immune tolerance comprises administering a PD-L1 hydrogel as described herein and the graft cell. In these embodiments, the graft cell is selected based on the condition to be treated. For example, when the subject is in need of the treatment or prevention of type 1 diabetes, the graft cell may be pancreatic islet cells. When the subject is in need of the treatment or prevention of allograft rejection, the graft cell may be cells from the allograft donor, such as allograft bone marrow cells, allograft cardiac myocytes and allograft vascular cells, or other cells from the allograft donor as discussed above. When the subject is in need of the treatment or prevention of xenograft rejection, the graft cell may be cells from the xenograft donor, such as xenograft bone marrow cells, xenograft cardiac myocytes and xenograft vascular cells, or other cells from the xenograft donor as discussed above. When the subject is in need of the treatment or prevention of autologous rejection, the graft cell may be autologous cells, such as cells derived from autologous tissue by induced pluripotency and differentiation of the induced pluripotent cells.

Thus, in some embodiments, the subject is in need of immune tolerance to a graft cell. In some embodiments, the graft cell is selected from PBMCs, bone marrow cells, hematopoietic stem cells, stein cells, mesenchymal stem cells, dendritic cells, dendritic cells pulsed with autoantigens, human beta cell products, and splenocytes. For example, when the subject is in need of the treatment or prevention of type 1 diabetes, the graft cell may be pancreatic islet cells, or in addition or alternatively other cells as discussed above. When the subject is in need of the treatment or prevention of allograft rejection, the graft cells may be cells from the allograft donor, such as cells selected from the group consisting of allograft bone marrow cells, allograft cardiac myocytes and allograft vascular cells, or other cells from the allograft donor as discussed above. When the subject is in need of the treatment or prevention of xenograft rejection, the graft cells may be cells from the xenograft donor, such as cells selected from the group consisting of xenograft bone marrow cells, xenograft cardiac myocytes and xenograft vascular cells, or other cells from the xenograft donor as discussed above. When the subject is need of treating or preventing autoimmunity, the graft cells may be (i) a cell expressing the autoantigen (ii) a cell decorated with the autoantigen and (iii) a dendritic cell pulsed with the autoantigen.

In accordance with these methods, the PD-L1 biomaterial (such as a PD-L1 hydrogel) and graft cell may be administered in the same composition, or may be administered separately. In some embodiments, the graft cell is encapsulated by the PD-L1 biomaterial. For example, the graft cell may be entrapped within the hydrogel or microgel biomaterial. In some embodiments, the PD-L1 biomaterial (such as a PD-L1 hydrogel) and graft cell are administered to the same site in the subject, such as by local injection into approximately the same site. In some embodiments, the PD-L1 biomaterial (such as a PD-L1 hydrogel) and graft cell are transplanted into the same site in the subject (e.g., co-transplantation). In accordance with any of these embodiments, the methods may achieve long-term, specific immunosuppression at the site of the graft.

Thus, in accordance with some embodiments, the administering is by transplantation. In some embodiments, allogeneic islet graft acceptance is achieved by simple co-transplantation of unmodified islets and PD-L1-presenting biomaterials without long term immunosuppression.

In some embodiments the PD-L1 biomaterial (such as a PD-L1 hydrogel) is administered with an additional therapeutic agent, such as an immunosuppressive drug, such as rapamycin or any of the others mentioned above. In such embodiments, the PD-L1 biomaterial (such as a PD-L1 hydrogel) and immunosuppressive drug may be formulated together (e.g., the hydrogel may comprise the immunosuppressive drug), or they may be administered in separate compositions, simultaneously or sequentially in any order. In some embodiments, a shorter course of immunosuppressive drug may be required than when no PD-L1 biomaterial is administered.

In some embodiments, PD-L1 biomaterials (such as a PD-L1 hydrogels) that comprise an immunosuppressive drug provide controlled release of the drug. In some embodiments, PD-L1 biomaterials (such as a PD-L1 hydrogels) that comprise an immunosuppressive drug provide controlled release of the drug within the graft microenvironment, or contain the graft in the form of a capsule engineered with these immunomodulatory molecules (PD-L1).

In some embodiments, administering a PD-L1 biomaterial (such as a PD-L1 hydrogel) as described herein with an immunosuppressive drug achieves a synergistic immunosuppressive effect. For example, in some embodiments, the immunosuppressive drug (such as rapamycin) works in synergy with PD-L1 to specifically eliminate pathogenic T effector cells while expanding T regulatory cells, thereby tipping the balance of immune response towards protection. Without being bound by theory, this synergistic effect may be achieved by the PD-L1 moiety activating death receptor-mediated extrinsic apoptosis in Teffector cells, while the immunosuppressive drug (such as rapamycin) activates mitochondria-mediated intrinsic apoptosis. See, e.g., Ju et al., Nature 373(6513): 444-448 (1995); and Yellen et al., *Cell Cycle,* 10(22): 3948-3956 (2011).

In some embodiments, administering a PD-L1 biomaterial (such as a PD-L1 hydrogel) as described herein with an immunosuppressive drug does not impair the systemic immune response, and may increase the ratio of T regulatory cells to T helper cells. T regulatory cells play an important role in modulating immune responses and they the inflammatory cues and infiltrate into rejecting grafts.

EXAMPLES

The following examples are for the purpose of illustration of the invention only and are not intended to limit the scope of the present invention in any manner whatsoever.

Example 1: SA-PD-L1 Fabrication

The N-terminus of the extracellular domain of mouse PD-L1 (68-728 bp, GI: AF233517.1, for example, as set forth in SEQ ID NO: 3) was linked to a modified form of core streptavidin (SA) (SEQ ID NO: 4) and a 6×His tag for purification. This sequence was then subcloned into the pMT/BiP/V5-His A CuSO4-inducible expression vector (Invitrogen) for stable expression in *Drosophila* S2 cells following previously published protocols. SA-PD-L1 protein (SEQ ID NO: 2 (mouse) and SEQ ID NO: 6 (human)) was purified using metal affinity chromatography and assessed for structure and purity using SDS-PAGE and Western blots.

Microgel Fabrication, Tethering of SA-PD-L1

Microgels were fabricated as previously described. Briefly, maleimide-terminated 4-arm poly(ethylene) glycol (PEG-4MAL) macromers (20 kDa, Laysan Bio) were reacted with 2.0 mM biotin-PEG-thiol (1 kDa, Nanocs) in PBS. The precursor was dispersed into 200 μm droplets and subsequently crosslinked with mineral oil (Sigma) containing 2% SPAN80 (Sigma) and a 1:15 emulsion of 30 mg/mL dithiothreitol (Sigma) within a flow-focusing microfluidic device.

Post-fabrication, microgels were washed 5 times in PBS containing 1% fetal bovine serum (FBS) (Hyclone). To assess biotinylation, 1000 microgels were incubated with streptavidin-AlexaFluor488 (Invitrogen) for 30 min in 100 μL PBS, and subsequently washed 3 times by centrifugation to remove unbound fluorescent streptavidin. 25 μL aliquots in triplicate from five different microgel runs were placed in a 24-well plate with a glass bottom and imaged using a BioTek Cytation 3 Imaging Plate reader (BioTek). Cellular analysis modality was implemented post-imaging to determine the size and fluorescence intensity of individual microgels.

SA-PD-L1 was labeled with AlexaFluor488 NHS ester (Thermo Fisher), followed by removal of free dye by desalting 3 times in Zeba columns (7 k MWCO, Thermo Fisher). Free protein fluorescence intensity, as well as the fluorescence intensity of tethered SA-PD-L1 to microgels, was assessed via a BioTek Synergy H4 microplate reader (BioTek).

For tethering SA-PD-L1, microgels were washed with PBS and transferred to FBS-coated conical tubes. SA-PD-L1 was added at 1 μg per 1000 microgels, followed by incubation for 2 h in a rotator at room temperature. Following incubation, microgels were pelleted, and the supernatant was removed for Western blot analysis; samples were rinsed twice with PBS to remove unbound protein. Western blot was performed on supernatant, control samples containing 1 μg of protein, or control samples at a similar concentration as the tethering samples. Western blot was analyzed by using a SuperSignal™ West Pico PLUS Chemiluminescent Substrate (ThermoFisher) in an Amersham Imager 600 (GE Healthcare). Polyclonal rabbit anti-human, mouse, and rat PD-L1 (ThermoFisher, PA520343, 1:2000), and an HRP goat anti-rabbit IgG (H+L) (ThermoFisher, 31460, 1:2000) were used for detection.

Binding Affinity of Chimeric Proteins

Fluorescence intensity of streptavidin (MP Biomedicals) and chimeric proteins (SA, SA-PD-L1) bound to biotin-4-fluorescein (B4F; Sigma) was measured by using a BioTek Synergy H4 microplate reader (BioTek) at room temperature in 150 μl of 50 mM Tris·HCl (fluorescence grade), 150 mM NaCl, 5 mM EDTA, 0.1 mg/ml bovine serum albumin (Sigma, A-9647), as described (20).

In Vitro Cytocompatibility of SA-PD-L1-Presenting Microgels

All animal procedures were performed under protocols approved by the Georgia Institute of Technology IACUC and following the National Institutes of Health guidelines. Rat pancreatic islets were isolated from Lewis male donors (250-300 g, Charles River) and cultured overnight at a density of 130 IEQ/$cm^2$. Cytocompatibility was performed as previously described (19). Briefly, 500 IEQ in 300 μL of complete CMRL were co-cultured with 1000 SA-PD-L1-presenting microgels for 24 h. Samples were analyzed for metabolic activity (MTT, Promega); Live/Dead (Viability/Cytotoxicity Kit; ThermoFisher); static glucose-stimulated insulin release (GSIR) (3 mM for Low, 11 mM high; measured via a Mercodia insulin kit); and multiplexed cytokine kit panel (Milliplex Rat Cytokine Panel with IFNg, IL-1b, IL-6, IL-17A, MCP-1, MIP-la). Whole-mount immunostaining analysis of insulin and glucagon was performed after fixation in 10% formalin. Samples were stained with antibodies against insulin (Dako, A0564, 1:100) or glucagon (Abcam, ab10988, 1:50) and co-stained with DAPI (Invitrogen, 1:500).

In Vitro Functional Assays

The bioactivity of soluble SA-PD-L1 was assessed via 1) T cell conversion assay; and 2) a proliferation assay. 1) Naïve CD4 cells were isolated from splenocytes of C57BL/6 mice using a BioLegend mouse naïve isolation kit. Cells were co-cultured in 96-well plates coated with 5 μg/mL anti-CD3 (BD Bioscience, 553058; clone: 145-2C11), and soluble 1 μg/mL of anti-CD28 (BD Bioscience, 553295; clone: 37.51). Groups consisted of: 1) cells with TGF-β(2 ng/mL; R&D Systems, 240B002); 2) cells with TGF-β and human IL-2 (20 U/mL; PeproTech, AF-200-02); 3) cells with SA-PD-L1 (5 μg per well) and IL-2; 4) cells with SA-PD-L1, TGF-β and IL-2. After 3 days in culture, cells were stained for live markers (Fixable Live/Dead Violet 1:1000; ThermoFisher), and fluorescent dye-conjugated antibodies against CD4 (PE-Cy7, 1:100 BD Bioscience, 563933, clone GK1.5), CD25 (APC, 1:100 BD Bioscience, 557192, clone PC61), and FoxP3 (PE, 1 μl per tube, BD Bioscience, 560414, clone MF23).

Proliferation assay was performed in a mixed lymphocyte reaction (MLR) on splenocytes harvested from 4 C mice (C57BL/6 transgenic for a TCR recognizing the BALB/c MHC I-Ad) co-cultured with irradiated splenocytes (2000 cGy) from BALB/c mice at a ratio of 1:30 4 C to irradiated BALB/c splenocytes. 24 h post-co-culture SA-PD-L1 (5 μg) (SEQ ID NO: 2) was added to corresponding wells; 56 h after starting cultures [3]-thymidine was added. Uptake of [3]-thymidine was measured with a scintillation counter.

In Vivo SA-PD-L1 Tracking

SA-PD-L1 was labeled with AlexaFluor750 NHS Ester (Thermo Fisher) as described (19). 1 μg of labeled protein was tethered to 1000 microgels. Microgels displaying SA-PD-L1 or free labeled protein were transplanted in the epidydimal fat pad (EFP) of non-diabetic BALB/c recipients (1200 microgels per EFP, n=4 SA-PD-L1-presenting microgels, n=5 free protein). Signal intensity was monitored over 20 days using an IVIS SpectrumCT imaging system (PerkinElmer). Intensity measurements were normalized to day 0 values.

In Vivo Phenotyping of Microgel Microenvironment

Microgels (600) functionalized with SA-PD-L1 (1 μg per 1000 microgels) or control microgels were transplanted in the epidydimal fat pat (EFP) of non-diabetic C57BL/6 with a dose of 200 IEQ BALB/c islets per EFP (n=4 per group). Seven days post-transplantation EFPs were removed and RNA was isolated using an RNeasy Lipid Tissue Mini Kit (Qiagen). RNA quality was assessed via NanoDrop 2000 (Thermo Fisher). A gene array for T Cell Anergy & Immune Tolerance was performed on samples following the manufacturer's instructions (Qiagen; $RT^2$ Profiler™ PCR Array Mouse T Cell Anergy & Immune Tolerance). qRT-PCR was performed on genes of interest (Table 1) using a High Capacity cDNA Reverse Transcription Kit (Thermo Fisher). Relative gene expression was quantified using TaqMan assays in QuantiStudio 6 flex (Life Technologies), normalized against β-actin. Relative expression was calculated by the ΔCt method, fold over the control microgels.

Multiparametric Flow Cytometry and CATALYST Analysis

Biotinylated microgels (1,200) conjugated with SA-PD-L1 (1 μg per 1000 microgels) or control microgels were transplanted in the EFPs of diabetic C57BL/6 with a dose of 600 IEQ BALB/c islets per EFP (n=4 for control and n=3 for SA-PD-L1). Animals were given rapamycin (LC Laboratories) every day post-transplantation for up to 15 days at 0.2 mg/kg. Seven days post-transplantation, epidydimal fat pads were removed and processed with collagenase to obtain single cells. Samples for lymphocyte panel were stained according to manufacturer instructions for CD45 (BioLegend, 103108), CD3e (BD, 561416), CD4 (BioLegend, 100412), CD8a (BioLegend, 100732), CD25 (BioLegend, 102016), FoxP3 (BD, 560408), CD44 (BD, 5560568), CD62L (BioLegend, 104440), PD1 (BD, 562523), Tim3 (BD, 742857), KLRG1 (BioLegend, 136419), Lag3 (BioLegend, 125227), zombie violet (BioLegend, 423113), PE Rat IgG2b, κ Isotype Control (BioLegend, 400607). Samples for myeloid panel were stained for CD45 (BioLegend, 103146), CD11b (BioLegend, 101228), CD11c (BioLegend, 117349), Ly6G (BioLegend, 127633), Ly6C (BioLegend, 128041), MHCII (BioLegend, 107652), CD11c (BioLegend, 11734), F4/80 (BioLegend, 123108), CD86 (BioLegend, 105012), CD206 (BioLegend, 141720), NK1.1 (BioLegend 108736), ICOS (BioLegend, 107706), PE Syrian Hamster IgG Isotype Ctrl Antibody (BioLegend, 402008), zombie violet (BioLegend, 423113). Samples were treated with FcR true block, and monocyte block reagents prior to staining (BioLegend 101319, 426102). FMOs and isotype controls for intracellular staining were run with every collection. Absolute cell counts were calculated based on precision count beads (BioLegend, 424902). FCS files were imported into FCS-Express, samples were gated for singlets by FSC-H FSC-A, SSC-H vs SSC-A discrimination, live cell population was gated based on zombie violet negative staining, followed by gating on CD3 and CD45 population. FCS files of this specific population was imported into an R package called CATALYST(40). The package implements a FlowSOM wrapper for high-resolution clustering, the same seed is fed every time to increase reproducibility. For visualization in two-dimensional space we implemented a tSNE function to a random subset of n cells per sample. FlowSOM generated clusters were exported from R as FCS files and imported into FCS express for visualization of MFI of specific markers for clusters of interest and their specific FMOs.

Dot Blot for Antibody Generation

A dot blot assay on serum samples were performed as follows: a nitrocellulose membrane was hydrated in 1% Tris-buffered saline (TBS), and the target protein (SA wild type, SA chimeric, SA-PD-L1, mouse IgG) and PEG solution were bound to the membrane using a vacuum-driven Manifold I Spot Blot System (Schleicher & Schuell). The membrane was dried for 10 min, followed by blocking with protein-free blocker (Thermo, Fisher). After washing 3 times with 1% TBS, diluted serum from 12 different animals (1:1000, 50-100 days post-transplantation) were passed through the membrane. Following washing, antibodies against the target protein were detected using an AlexaFluor-680 or AlexaFluor 488 labeled rabbit anti-mouse IgG (Thermo Fisher). The blot was imaged using a Licor Odyssey gel imager. Blot intensity was then quantified using the protein array analysis plug-in from ImageJ. Positive blots were determined to be five times the average intensity of background controls (2% BSA).

Islet Transplantation

BALB/c or C57BL/6 pancreatic islets were isolated using Liberase TFlex as a digestive enzyme (Roche Life Science) and purified by a Ficoll density gradient (Corning). For syngeneic transplantation 600 IEQ with microgels were transplanted into a single EFP of STZ diabetic recipients (n=6) and sealed with a PEG VEGF hydrogel(28), control subjects for syngeneic transplants refer to historical controls used for internal quality control of islet isolations. For allogeneic studies naked BALB/c islets were co-transplanted either with unmodified microgels with no rapamycin treatment (n=5), free SA-PD-L1 with rapamycin treatment (n=6), unmodified microgels with rapamycin treatment (n=14), SA-PD-L1-presenting microgels with no rapamycin treatment (n=9), SA-presenting microgels with rapamycin treatment (n=7), and SA-PD-L1-presenting microgels with rapamycin treatment (n=12). Streptozotocin (STZ, sigma) induced diabetic C57BL/6, 175 mg/kg, were used as recipients if blood sugar (BG) >350 mg/dL for 3 consecutive readings. Transplantation into the EFP was performed as previously described(19). Briefly, islets were transplanted in a ratio of 1 IEQ:2 microgel into the EFP of STZ-induced diabetic C57BL/6, which was then sealed with an in situ crosslinked PEG hydrogel containing VEGF(28). For a subset of animals, rapamycin (LC laboratories) was administered intraperitoneal for 15 days at 0.2 mg/kg starting the day of surgery. IPGTT was performed on day 30 post-transplantation after 6 h fasting using a 2 g/kg glucose solution (25%).

For a group of recipients (5 mice/group), blood samples were collected at 50-70 days post-transplantation for serum analysis. Blinded blood samples were deposited in serum separator tubes and sent to ANTECH Diagnostics for analysis. Full necropsies were also performed for evidence of any gross abnormalities post-transplantation. Explanted kidneys, livers, lungs and spleens were preserved in 10% neutral formalin solution (Sigma) and processed and stained with hematoxylin and eosin. Microscopy was performed using an optical microscope (Zeiss 510), and the images were taken using Axio Vision software. Images presented are representative of all samples collected (n=10 mice/group).

For a subset of recipients (5 mice/group), grafts were explanted at day 3 post-transplantation and immunophenotyping was performed as described above.

MLR was performed on splenocytes from naïve, diabetic, and animals transplanted with control, SA-, or SA-PD-L1-presenting microgels that had received rapamycin. Splenocytes were labeled with CellTrace Violet and used as responders against alloantigens. The cultures were harvested 4 days later and run on a BD Aria flow cytometer to assess the proliferation of CD4+ and CD8+ T cells by gating on stained cells.

Diabetes reversal due to treatment and not spontaneous regeneration of β-cell function was confirmed in a subset of long-term recipients by survival graft explants and total pancreatectomy. Insulin from the extracted pancreas was measured via a MERCODIA Insulin ELISA kit.

Explanted grafts were fixed in 10% formalin and embedded in paraffin blocks for immunohistochemical analysis. Slides were stained for insulin (Dako A0564, 1:100), glucagon (Abcam ab10988, 1:50), FoxP3 (NobusBio NB100-39002AF488, 1:100), CD3 (Abcam ab16669, 1:100), and DAPI (Invitrogen D1306, 1:500). Histological images were collected using a Zeiss LSM 710 confocal microscope. Isotype controls were used for antibodies of interest as seen in Figure S5. H&E and trichrome was performed following standard protocols.

Statistical Analyses: Individual data points are plotted with error bars indicating standard deviation (S.D.) unless indicated in the figure legend. Experiments were repeated at least twice, and the numbers of replicates are indicated in figure legends. Animals were randomized and blinded among the control and treatment groups. Treated diabetic animals that did not achieve primary function (defined as 3 consecutive blood glucose readings <250 mg/dL) were excluded from analysis as this is variability in the islet quality and not the experimental treatment. Blood glucose measurements were performed on the indicated day before noon by blinded and non-blinded personnel in a randomized fashion. The sample size for each experimental group and the statistical test used to determine significant differences among groups are reported in the appropriate figure legend. Non-linear single exponential decay curve fits were performed in GraphPad Prism and retention time was compared using a mix effects model (REML). Survival curves were analyzed using a Mantel-Cox test. GraphPad Prism 8 was used for data analysis and representation, and $p<0.05$ was considered statistically significant.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

| SEQUENCES |
|---|
| SEQ ID NO: 1: Mouse SA-PDL1 Construct-External Domain with C-terminal SA and 6xHis<br>AGATCTGCGTTTACTATCACGGCTCCAAAGGACTTGTACGTGGTGGAGTATGGCA<br>GCAACGTCACGATGGAGTGCAGATTCCCTGTAGAACGGGAGCTGGACCTGCTTG<br>CGTTAGTGGTGTACTGGGAAAAGGAAGATGAGCAAGTGATTCAGTTTGTGGCAG<br>GAGAGGAGGACCTTAAGCCTCAGCACAGCAACTTCAGGGGGAGAGCCTCGCTGC<br>CAAAGGACCAGCTTTTGAAGGGAAATGCTGCCCTTCAGATCACAGACGTCAAGC<br>TGCAGGACGCAGGCGTTTACTGCTGCATAATCAGCTACGGTGGTGCGGACTACA<br>AGCGAATCACGCTGAAAGTCAATGCCCCATACCGCAAAATCAACCAGAGAATTT<br>CCGTGGATCCAGCCACTTCTGAGCATGAACTAATATGTCAGGCCGAGGGTTATCC<br>AGAAGCTGAGGTAATCTGGACAAACAGTGACCACCAACCCGTGAGTGGGAAGA<br>GAAGTGTCACCACTTCCCGGACAGAGGGGATGCTTCTCAATGTGACCAGCAGTCT<br>GAGGGTCAACGCCACAGCGAATGATGTTTTCTACTGTACGTTTTGGAGATCACAG<br>CCAGGGCAAAACCACACAGCGGAGCTGATCATCCCAGAACTGCCTGCAACACAT<br>CCTCCACAGAACAGGAGATCTGCTGAAGCTGCAGCTAAAGAAGCTGCAGCTAAA<br>GCTGCTGCTGGTACCATCACCGGCACCTGGTACAACCAGCTCGGCTCGACCTTCA<br>TCGTGACCGCGGGCGCCGATGGCGCCCTGACCGGAACCTACGAGTCGGCCGTCG<br>GCAACGCCGAGAGCCGCTACGTCCTGACCGGTCGTTACGACAGCGCCCCGGCCA<br>CCGACGGCAGCGGCACCGCCCTCGGTTGGACGGTGGCCTGGAAGAATAACTACC<br>GCAACGCCCACTCCGCGACCACGTGGAGCGGCCAGTACGTCGGCGGCGCCGAGG<br>CGAGGATCAACACCCAGTGGCTGTTGACCTCCGGCGCCACCGAGGCCAACGCCT<br>GGAAGTCCACGCTGGTCGGCCACGACACCTTCACCAAGGTGAAGCCGTCCGCCG<br>CCTCAAGCGGAGGCGGTGGATCAGGTGGAGGCGAATTCCATCATCACCATCACC<br>ATTAATAGCTCGAG |
| SEQ ID NO: 2: Protein sequence for Mouse SA-PDL1 Construct-External Domain with C-terminal SA and 6xHis<br>RSAFTITAPKDLYVVEYGSNVTMECRFPVERELDLLALVVYWEKEDEQVIQFVAGEE<br>DLKPQHSNFRGRASLPKDQLLKGNAALQITDVKLQDAGVYCCIISYGGADYKRITLK<br>VNAPYRKINQRISVDPATSEHELICQAEGYPEAEVIWTNSDHQPVSGKRSVTTSRTEG<br>MLLNVTSSLRVNATANDVFYCTFWRSQPGQNHTAELIIPELPATHPPQNRRSAEAAA<br>KEAAAKAAAGTITGTWYNQLGSTFIVTAGADGALTGTYESAVGNAESRYVLTGRYD<br>SAPATDGSGTALGWTVAWKNNYRNAHSATTWSGQYVGGAEARINTQWLLTSGAT<br>EANAWKSTLVGHDTFTKVKPSAASSGGGGSGGGEFHHHHHH |
| SEQ ID NO: 3 Protein sequence for Mouse PD-L1<br>FTITAPKDLYVVEYGSNVTMECRFPVERELDLLALVVYWEKEDEQVIQFVAGEEDL<br>KPQHSNFRGRASLPKDQLLKGNAALQITDVKLQDAGVYCCIISYGGADYKRITLKVN<br>APYRKINQRISVDPATSEHELICQAEGYPEAEVIWTNSDHQPVSGKRSVTTSRTEGML<br>LNVTSSLRVNATANDVFYCTFWRSQPGQNHTAELIIPELPATHPPQNR |
| SEQ ID NO: 4: protein sequence for streptavidin<br>ITGTWYNQLGSTFIVTAGADGALTGTYESAVGNAESRYVLTGRYDSAPATDGSGTA<br>LGWTVAWKNNYRNAHSATTWSGQYVGGAEARINTQWLLTSGATEANAWKSTLVG<br>HDTFTKVKPSAASS |
| SEQ ID NO: 5: Human SA-PDL1 Construct-External Domain with C-terminal SA and 6xHis<br>AGATCTTTTACTGTCACGGTTCCCAAGGACCTATATGTGGTAGAGTATGGTAGCA<br>ATATGACAATTGAATGCAAATTCCCAGTAGAAAAACAATTAGACCTGGCTGCAC<br>TAATTGTCTATTGGGAAATGGAGGATAAGAACATTATTCAATTTGTGCATGGAGA |

-continued

SEQUENCES

GGAAGACCTGAAGGTTCAGCATAGTAGCTACAGACAGAGGGCCCGGCTGTTGAA
GGACCAGCTCTCCCTGGGAAATGCTGCACTTCAGATCACAGATGTGAAATTGCA
GGATGCAGGGGTGTACCGCTGCATGATCAGCTATGGTGGTGCCGACTACAAGCG
AATTACTGTGAAAGTCAATGCCCCATACAACAAAATCAACCAAAGAATTTTGGTT
GTGGATCCAGTCACCTCTGAACATGAACTGACATGTCAGGCTGAGGGCTACCCC
AAGGCCGAAGTCATCTGGACAAGCAGTGACCATCAAGTCCTGAGTGGTAAGACC
ACCACCACCAATTCCAAGAGAGAGGAGAAGCTTTTCAATGTGACCAGCACACTG
AGAATCAACACAACAACTAATGAGATTTTCTACTGCACTTTTAGGAGATTAGATC
CTGAGGAAAACCATACAGCTGAATTGGTCATCCCAGAACTACCTCTGGCACATCC
TCCAAATGAAAGGGCTGAAGCTGCAGCTAAAGAAGCTGCAGCTAAAGCTGCTGC
TGGTACCATCACCGGCACCTGGTACAACCAGCTCGGCTCGACCTTCATCGTGACC
GCGGGCGCCGATGGCGCCCTGACCGGAACCTACGAGTCGGCCGTCGGCAACGCC
GAGAGCCGCTACGTCCTGACCGGTCGTTACGACAGCGCCCCGGCCACCGACGGC
AGCGGCACCGCCCTCGGTTGGACGGTGGCCTGGAAGAATAACTACCGCAACGCC
CACTCCGCGACCACGTGGAGCGGCCAGTACGTCGGCGGCGCCGAGGCGAGGATC
AACACCCAGTGGCTGTTGACCTCCGGCGCCACCGAGGCCAACGCCTGGAAGTCC
ACGCTGGTCGGCCACGACACCTTCACCAAGGTGAAGCCGTCCGCCGCCTCAAGC
GGAGGCGGTGGATCAGGTGGAGGCGAATTCCATCATCACCATCACCATTAATAG
CTCGAG

SEQ ID NO: 6: Protein sequence for Human SA-PDL1 Construct-External Domain with C-terminal SA and 6xHis
RSFTVTVPKDLYVVEYGSNMTIECKFPVEKQLDLAALIVYWEMEDKNIIQFVHGEED
LKVQHSSYRQRARLLKDQLSLGNAALQITDVKLQDAGVYRCMISYGGADYKRITVK
VNAPYNKINQRILVVDPVTSEHELTCQAEGYPKAEVIWTSSDHQVLSGKTTTTNSKR
EEKLFNVTSTLRINTTTNEIFYCTFRRLDPEENHTAELVIPELPLAHPPNERAEAAAKE
AAAKAAAGTITGTWYNQLGSTFIVTAGADGALTGTYESAVGNAESRYVLTGRYDSA
PATDGSGTALGWTVAWKNNYRNAHSATTWSGQYVGGAEARINTQWLLTSGATEA
NAWKSTLVGHDTFTKVKPSAASSGGGGSGGGEFHHHHHH SEQ ID NO: 7 protein sequence for human PDL1
FTVTVPKDLYVVEYGSNMTIECKFPVEKQLDLAALIVYWEMEDKNIIQFVHGEEDLK
VQHSSYRQRARLLKDQLSLGNAALQITDVKLQDAGVYRCMISYGGADYKRITVKVN
APYNKINQRILVVDPVTSEHELTCQAEGYPKAEVIWTSSDHQVLSGKTTTTNSKREE
KLFNVTSTLRINTTTNEIFYCTFRRLDPEENHTAELVIPELPLAHPPNER

What is claimed is:

1. A three-dimensional PD-L1 presenting composition comprising a hydrogel network conjugated to PD-L1 via a biotin/streptavidin complex, wherein the hydrogel is covalently bound to a plurality of biotin residues, the PD-L1 is conjugated to streptavidin; and wherein the composition further comprises an immunosuppressant.

2. The PD-L1 presenting composition according to claim 1, wherein the immunosuppressant comprises rapamycin, cyclophosamide busulfan, fludarabine, methotrexate, sulfasalazine, hydroxychloroquine, azathioprine, tocilizumab, etanercept, adalimumab, anakinra, abatacept, rituximab, certolizumab, golimumab, cyclosporine, dexamethasone, methylprednisolone, prednisone, tacrolimus, and/or triamcinolone.

3. The PD-L1 presenting composition according to claim 1, wherein the immunosuppressant comprises rapamycin.

4. The PD-L1 presenting composition according to claim 1, wherein the hydrogel network composition comprises crosslinked hydrophilic polymers.

5. The PD-L1 presenting composition according to claim 1, wherein the hydrogel network composition comprises crosslinked polyethylene glycol.

6. The PD-L1 presenting composition according to claim 1, wherein the hydrogel network composition has the general formula:

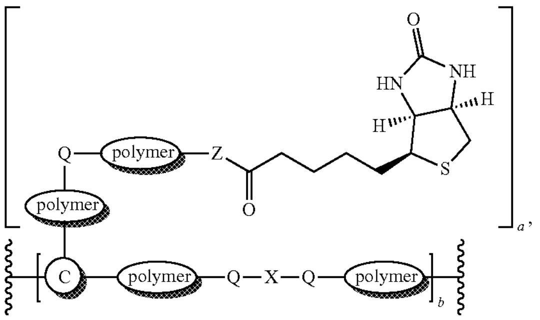

wherein 'polymer' in each case independently represents a hydrophilic polymer, the encircled C represents a core, Q represents a linker, X represents a crosslinker, Z is null or a linker, and the sum of a+b is from 3-10.

7. The PD-L1 presenting composition according to claim 6, wherein the hydrogel network has the general formula:

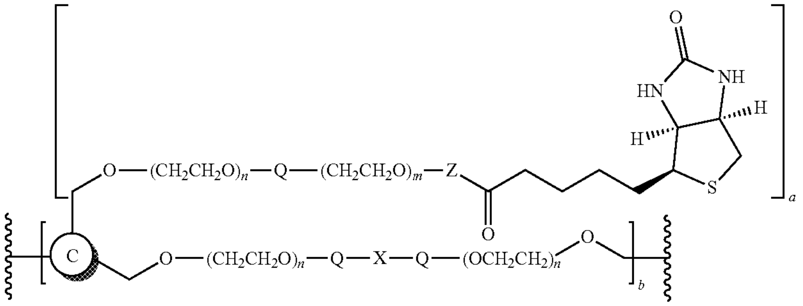

and each of n and m is independently selected from an integer from 10-50,000.

8. The PD-L1 presenting composition according to claim 7, wherein n is in each case an integer from 15-30,000.

9. The PD-L1 presenting composition according to claim 7, wherein each $-(CH_2CH_2O)_n-$ unit can have an average molecular weight from 1,000-50,000.

10. The PD-L1 presenting composition according to claim 7, wherein m is an integer from 10-1,000.

11. The PD-L1 presenting composition according to claim 7, wherein each $-(CH_2CH_2O)_m-$ unit can have an average molecular weight from 250-50,000.

12. The PD-L1 presenting composition according to claim 6, wherein core can have the general structure:

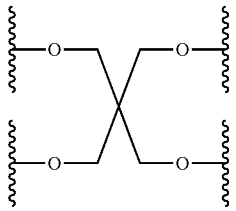

or

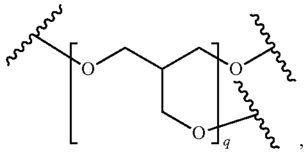

, wherein q is an integer from 1-10 and ⦚ represents a link to the hydrophilic polymer.

13. The PD-L1 presenting composition according to claim 6, wherein Q has the formula:

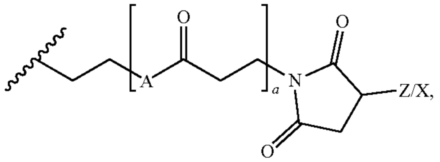

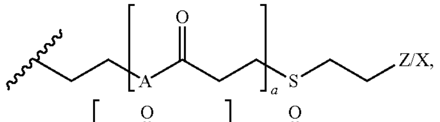

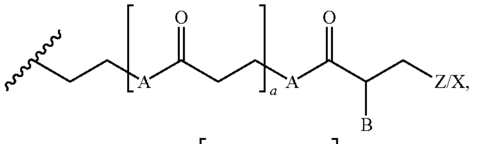

or

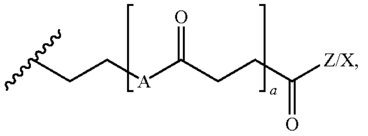

wherein A is independently selected from O or NH, a is independently selected from 0 or 1, B is selected from hydrogen or methyl, and ⦚ represents a link to the hydrophilic polymer.

14. The PD-L1 presenting composition of claim 1, prepared by a process including the step of reacting a compound of Formula (I):

[Formula (1)]

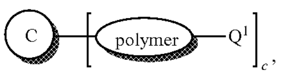

wherein $Q^1$ comprises an electrophilic group, and c is the sum of a+b, with a compound of Formula (2):

[Formula (2)]

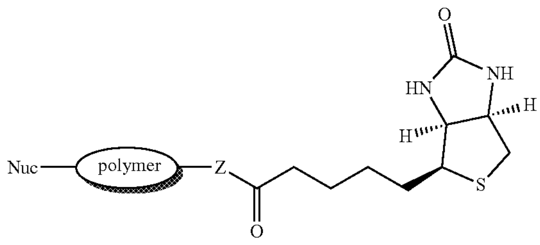

wherein 'Nuc' is a nucleophilic group capable of reacting the $Q^1$, to form a compound of Formula (3):

[Formula (3)]

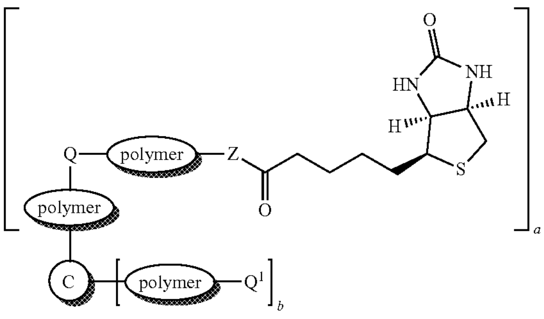

15. The PD-L1 presenting composition according to claim 14, wherein the molar ratio of the compound of Formula (1) to the compound of Formula (2) is from 10:1 to 1:10.

16. The PD-L1 presenting composition according to claim 14, further comprising the step of reacting the compound of Formula (3) with a crosslinker to give the hydrogel network composition having the formula:

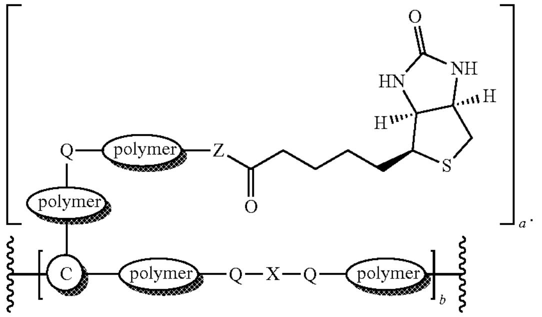

wherein X represents a crosslinker.

17. The PD-L1 presenting composition according to claim 16, wherein the crosslinker has the formula:

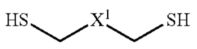 or 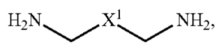

wherein $X^1$ is a is a $C_{1-8}$alkylene group, optionally substituted one or more times by OH, or $X^1$ is a poly (ethylene)glycol group having from 1 to 20 monomer units.

18. The PD-L1 presenting composition according to claim 17, wherein the crosslinker has the formula:

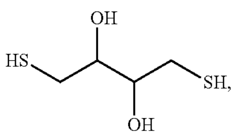

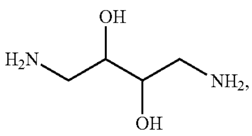

-continued

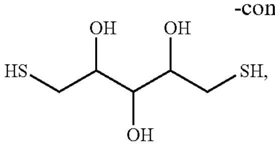

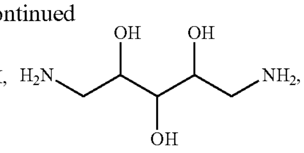

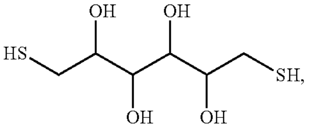 or

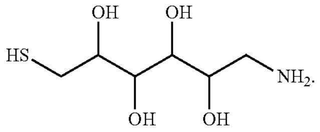

19. The PD-L1 presenting composition according to claim 6, prepared by further incubating the hydrogel network composition having the formula:

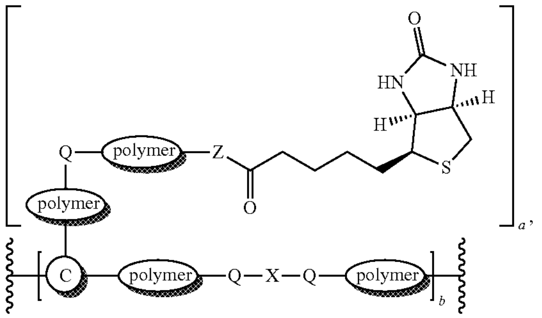

with SA-PD-L1.

20. A method of effecting immunomodulation comprising administering to a patient in need thereof the PD-L1 presenting composition according to claim 1.

* * * * *

SEQUENCE LISTING

<160> NUMBER OF SEQ ID NOS: 7

<210> SEQ ID NO 1
<211> LENGTH: 1164
<212> TYPE: DNA
<213> ORGANISM: Artificial Sequence
<220> FEATURE:
<223> OTHER INFORMATION: Synthetic construct

<400> SEQUENCE: 1
agatctgcgt ttactatcac ggctccaaag gacttgtacg tggtggagta tggcagcaac 60
gtcacgatgg agtgcagatt ccctgtagaa cgggagctgg acctgcttgc gttagtggtg 120
tactgggaaa aggaagatga gcaagtgatt cagtttgtgg caggagagga ggaccttaag 180
cctcagcaca gcaacttcag gggagagcc tcgctgccaa aggaccagct tttgaaggga 240
aatgctgccc ttcagatcac agacgtcaag ctgcaggacg caggcgttta ctgctgcata 300
atcagctacg gtggtgcgga ctacaagcga atcacgctga aagtcaatgc cccataccgc 360
aaaatcaacc agagaatttc cgtggatcca gccacttctg agcatgaact aatatgtcag 420
gccgagggtt atccagaagc tgaggtaatc tggacaaaca gtgaccacca acccgtgagt 480
gggaagagaa gtgtcaccac ttcccggaca gaggggatgc ttctcaatgt gaccagcagt 540
ctgagggtca acgccacagc gaatgatgtt ttctactgta cgttttggag atcacagcca 600
gggcaaaacc acacagcgga gctgatcatc ccagaactgc ctgcaacaca tcctccacag 660
aacaggagat ctgctgaagc tgcagctaaa gaagctgcag ctaaagctgc tgctggtacc 720

-continued

```
atcaccggca cctggtacaa ccagctcggc tcgaccttca tcgtgaccgc gggcgccgat    780

ggcgccctga ccggaaccta cgagtcggcc gtcggcaacg ccgagagccg ctacgtcctg    840

accggtcgtt acgacagcgc cccggccacc gacggcagcg gcaccgccct cggttggacg    900

gtggcctgga agaataacta ccgcaacgcc cactccgcga ccacgtggag cggccagtac    960

gtcggcggcg ccgaggcgag gatcaacacc cagtggctgt tgacctccgg cgccaccgag   1020

gccaacgcct ggaagtccac gctggtcggc cacgacacct tcaccaaggt gaagccgtcc   1080

gccgcctcaa gcggaggcgg tggatcaggt ggaggcgaat tccatcatca ccatcaccat   1140

taatagctcg agtaatagct cgag                                          1164
```

```
<210> SEQ ID NO 2
<211> LENGTH: 380
<212> TYPE: PRT
<213> ORGANISM: Artificial Sequence
<220> FEATURE:
<223> OTHER INFORMATION: Synthetic construct

<400> SEQUENCE: 2

Arg Ser Ala Phe Thr Ile Thr Ala Pro Lys Asp Leu Tyr Val Val Glu
1               5                   10                  15

Tyr Gly Ser Asn Val Thr Met Glu Cys Arg Phe Pro Val Glu Arg Glu
            20                  25                  30

Leu Asp Leu Leu Ala Leu Val Val Tyr Trp Glu Lys Glu Asp Glu Gln
        35                  40                  45

Val Ile Gln Phe Val Ala Gly Glu Glu Asp Leu Lys Pro Gln His Ser
    50                  55                  60

Asn Phe Arg Gly Arg Ala Ser Leu Pro Lys Asp Gln Leu Leu Lys Gly
65                  70                  75                  80

Asn Ala Ala Leu Gln Ile Thr Asp Val Lys Leu Gln Asp Ala Gly Val
                85                  90                  95

Tyr Cys Cys Ile Ile Ser Tyr Gly Gly Ala Asp Tyr Lys Arg Ile Thr
            100                 105                 110

Leu Lys Val Asn Ala Pro Tyr Arg Lys Ile Asn Gln Arg Ile Ser Val
        115                 120                 125

Asp Pro Ala Thr Ser Glu His Glu Leu Ile Cys Gln Ala Glu Gly Tyr
    130                 135                 140

Pro Glu Ala Glu Val Ile Trp Thr Asn Ser Asp His Gln Pro Val Ser
145                 150                 155                 160

Gly Lys Arg Ser Val Thr Thr Ser Arg Thr Glu Gly Met Leu Leu Asn
                165                 170                 175

Val Thr Ser Ser Leu Arg Val Asn Ala Thr Ala Asn Asp Val Phe Tyr
            180                 185                 190

Cys Thr Phe Trp Arg Ser Gln Pro Gly Gln Asn His Thr Ala Glu Leu
        195                 200                 205

Ile Ile Pro Glu Leu Pro Ala Thr His Pro Pro Gln Asn Arg Arg Ser
    210                 215                 220

Ala Glu Ala Ala Ala Lys Glu Ala Ala Ala Lys Ala Ala Ala Gly Thr
225                 230                 235                 240

Ile Thr Gly Thr Trp Tyr Asn Gln Leu Gly Ser Thr Phe Ile Val Thr
                245                 250                 255

Ala Gly Ala Asp Gly Ala Leu Thr Gly Thr Tyr Glu Ser Ala Val Gly
            260                 265                 270

Asn Ala Glu Ser Arg Tyr Val Leu Thr Gly Arg Tyr Asp Ser Ala Pro
        275                 280                 285
```

-continued

```
Ala Thr Asp Gly Ser Gly Thr Ala Leu Gly Trp Thr Val Ala Trp Lys
    290                 295                 300

Asn Asn Tyr Arg Asn Ala His Ser Ala Thr Thr Trp Ser Gly Gln Tyr
305                 310                 315                 320

Val Gly Gly Ala Glu Ala Arg Ile Asn Thr Gln Trp Leu Leu Thr Ser
                325                 330                 335

Gly Ala Thr Glu Ala Asn Ala Trp Lys Ser Thr Leu Val Gly His Asp
            340                 345                 350

Thr Phe Thr Lys Val Lys Pro Ser Ala Ala Ser Ser Gly Gly Gly Gly
        355                 360                 365

Ser Gly Gly Gly Glu Phe His His His His His His
    370                 375                 380


<210> SEQ ID NO 3
<211> LENGTH: 219
<212> TYPE: PRT
<213> ORGANISM: Mouse

<400> SEQUENCE: 3

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg
    210                 215


<210> SEQ ID NO 4
<211> LENGTH: 124
<212> TYPE: PRT
<213> ORGANISM: Artificial Sequence
<220> FEATURE:
<223> OTHER INFORMATION: Synthetic construct

<400> SEQUENCE: 4
```

```
Ile Thr Gly Thr Trp Tyr Asn Gln Leu Gly Ser Thr Phe Ile Val Thr
1               5                   10                  15

Ala Gly Ala Asp Gly Ala Leu Thr Gly Thr Tyr Glu Ser Ala Val Gly
            20                  25                  30

Asn Ala Glu Ser Arg Tyr Val Leu Thr Gly Arg Tyr Asp Ser Ala Pro
        35                  40                  45

Ala Thr Asp Gly Ser Gly Thr Ala Leu Gly Trp Thr Val Ala Trp Lys
    50                  55                  60

Asn Asn Tyr Arg Asn Ala His Ser Ala Thr Thr Trp Ser Gly Gln Tyr
65                  70                  75                  80

Val Gly Gly Ala Glu Ala Arg Ile Asn Thr Gln Trp Leu Leu Thr Ser
                85                  90                  95

Gly Ala Thr Glu Ala Asn Ala Trp Lys Ser Thr Leu Val Gly His Asp
            100                 105                 110

Thr Phe Thr Lys Val Lys Pro Ser Ala Ala Ser Ser
        115                 120


<210> SEQ ID NO 5
<211> LENGTH: 1146
<212> TYPE: DNA
<213> ORGANISM: Artificial Sequence
<220> FEATURE:
<223> OTHER INFORMATION: Synthetic construct

<400> SEQUENCE: 5

agatctttta ctgtcacggt tcccaaggac ctatatgtgg tagagtatgg tagcaatatg      60

acaattgaat gcaaattccc agtagaaaaa caattagacc tggctgcact aattgtctat     120

tgggaaatgg aggataagaa cattattcaa tttgtgcatg gagaggaaga cctgaaggtt     180

cagcatagta gctacagaca gagggcccgg ctgttgaagg accagctctc cctgggaaat     240

gctgcacttc agatcacaga tgtgaaattg caggatgcag gggtgtaccg ctgcatgatc     300

agctatggtg gtgccgacta caagcgaatt actgtgaaag tcaatgcccc atacaacaaa     360

atcaaccaaa gaattttggt tgtggatcca gtcacctctg aacatgaact gacatgtcag     420

gctgagggct accccaaggc cgaagtcatc tggacaagca gtgaccatca agtcctgagt     480

ggtaagacca ccaccaccaa ttccaagaga gaggagaagc ttttcaatgt gaccagcaca     540

ctgagaatca acacaacaac taatgagatt ttctactgca cttttaggag attagatcct     600

gaggaaaacc atacagctga attggtcatc ccagaactac ctctggcaca tcctccaaat     660

gaaagggctg aagctgcagc taaagaagct gcagctaaag ctgctgctgg taccatcacc     720

ggcacctggt acaaccagct cggctcgacc ttcatcgtga ccgcgggcgc cgatggcgcc     780

ctgaccggaa cctacgagtc ggccgtcggc aacgccgaga gccgctacgt cctgaccggt     840

cgttacgaca gcgccccggc caccgacggc agcggcaccg ccctcggttg gacggtggcc     900

tggaagaata actaccgcaa cgcccactcc gcgaccacgt ggagcggcca gtacgtcggc     960

ggcgccgagg cgaggatcaa cacccagtgg ctgttgacct ccggcgccac cgaggccaac    1020

gcctggaagt ccacgctggt cggccacgac accttcacca aggtgaagcc gtccgccgcc    1080

tcaagcggag gcggtggatc aggtggaggc gaattccatc atcaccatca ccattaatag    1140

ctcgag                                                               1146


<210> SEQ ID NO 6
<211> LENGTH: 378
<212> TYPE: PRT
<213> ORGANISM: Artificial Sequence
```

-continued

<220> FEATURE:
<223> OTHER INFORMATION: Synthetic construct

<400> SEQUENCE: 6

```
Arg Ser Phe Thr Val Thr Val Pro Lys Asp Leu Tyr Val Val Glu Tyr
1               5                   10                  15

Gly Ser Asn Met Thr Ile Glu Cys Lys Phe Pro Val Glu Lys Gln Leu
            20                  25                  30

Asp Leu Ala Ala Leu Ile Val Tyr Trp Glu Met Glu Asp Lys Asn Ile
        35                  40                  45

Ile Gln Phe Val His Gly Glu Glu Asp Leu Lys Val Gln His Ser Ser
    50                  55                  60

Tyr Arg Gln Arg Ala Arg Leu Leu Lys Asp Gln Leu Ser Leu Gly Asn
65                  70                  75                  80

Ala Ala Leu Gln Ile Thr Asp Val Lys Leu Gln Asp Ala Gly Val Tyr
                85                  90                  95

Arg Cys Met Ile Ser Tyr Gly Gly Ala Asp Tyr Lys Arg Ile Thr Val
            100                 105                 110

Lys Val Asn Ala Pro Tyr Asn Lys Ile Asn Gln Arg Ile Leu Val Val
        115                 120                 125

Asp Pro Val Thr Ser Glu His Glu Leu Thr Cys Gln Ala Glu Gly Tyr
    130                 135                 140

Pro Lys Ala Glu Val Ile Trp Thr Ser Ser Asp His Gln Val Leu Ser
145                 150                 155                 160

Gly Lys Thr Thr Thr Thr Asn Ser Lys Arg Glu Glu Lys Leu Phe Asn
                165                 170                 175

Val Thr Ser Thr Leu Arg Ile Asn Thr Thr Thr Asn Glu Ile Phe Tyr
            180                 185                 190

Cys Thr Phe Arg Arg Leu Asp Pro Glu Glu Asn His Thr Ala Glu Leu
        195                 200                 205

Val Ile Pro Glu Leu Pro Leu Ala His Pro Pro Asn Glu Arg Ala Glu
    210                 215                 220

Ala Ala Ala Lys Glu Ala Ala Ala Lys Ala Ala Ala Gly Thr Ile Thr
225                 230                 235                 240

Gly Thr Trp Tyr Asn Gln Leu Gly Ser Thr Phe Ile Val Thr Ala Gly
                245                 250                 255

Ala Asp Gly Ala Leu Thr Gly Thr Tyr Glu Ser Ala Val Gly Asn Ala
            260                 265                 270

Glu Ser Arg Tyr Val Leu Thr Gly Arg Tyr Asp Ser Ala Pro Ala Thr
        275                 280                 285

Asp Gly Ser Gly Thr Ala Leu Gly Trp Thr Val Ala Trp Lys Asn Asn
    290                 295                 300

Tyr Arg Asn Ala His Ser Ala Thr Thr Trp Ser Gly Gln Tyr Val Gly
305                 310                 315                 320

Gly Ala Glu Ala Arg Ile Asn Thr Gln Trp Leu Leu Thr Ser Gly Ala
                325                 330                 335

Thr Glu Ala Asn Ala Trp Lys Ser Thr Leu Val Gly His Asp Thr Phe
            340                 345                 350

Thr Lys Val Lys Pro Ser Ala Ala Ser Ser Gly Gly Gly Gly Ser Gly
        355                 360                 365

Gly Gly Glu Phe His His His His His His
    370                 375
```

<210> SEQ ID NO 7

-continued

```
<211> LENGTH: 220
<212> TYPE: PRT
<213> ORGANISM: Homo sapiens

<400> SEQUENCE: 7

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220
```